(12) United States Patent
Mederski et al.

(10) Patent No.: US 7,829,566 B2
(45) Date of Patent: Nov. 9, 2010

(54) 4-AMINO-QUINAZOLINES

(76) Inventors: Werner Mederski, Katzenelnbogenweg 1, Zwingenberg (DE) 64673; Ralf Devant, Frankfurter Landstrasse 135, Darmstadt (DE) 64291; Gerhard Barnickel, Emilstrasse 27, Darmstadt (DE) 64293; Sabine Bernotat-Danielowski, Liebigstrasse 5, Bad Nauheim (DE) 61231; James Vickers, 4 Haldane Road, Caversham, Reading RG4 7PS (GB); Bertram Cezanne, Goethestrasse 47, 64546 Mörfelden-Walldorf (DE); Daljit Dhanoa, 2037 Skiles Blvd., West Chester, PA (US) 19382; Bao-Ping Zhao, 3606 Hunters Glen Dr., Plainsboro, NJ (US) 08536; James Rinker, 1115 Fern Ave., Kenhurst, PA (US) 19607; Mark R. Player, 5022 Swan Dr., Phoenixville, PA (US) 19460; Edward Jaeger, 210 Kelso Cir., Trappe, PA (US) 19426; Richard Soll, 324 Glenn Ave., Lawrenceville, NJ (US) 08648

( * ) Notice: Subject to any disclaimer, the term of this patent is extended or adjusted under 35 U.S.C. 154(b) by 1364 days.

(21) Appl. No.: 11/300,626

(22) Filed: Dec. 14, 2005

(65) Prior Publication Data

US 2007/0293667 A1    Dec. 20, 2007

Related U.S. Application Data

(63) Continuation of application No. 10/380,909, filed as application No. PCT/EP01/10704 on Sep. 17, 2001, now abandoned.

(51) Int. Cl.
  *A61K 31/497* (2006.01)
  *A61K 31/517* (2006.01)
  *A61K 31/535* (2006.01)
  *C07D 239/84* (2006.01)
  *C07D 413/10* (2006.01)

(52) U.S. Cl. .................. 514/252.14; 514/234.5; 514/266.22; 514/266.4; 544/116; 544/293

(58) Field of Classification Search ............ 514/252.14, 514/266.22, 266.4, 234.5; 544/293, 116
  See application file for complete search history.

(56) References Cited

U.S. PATENT DOCUMENTS

| 3,753,981 | A | 8/1973 | Breuer |
|---|---|---|---|
| 3,970,648 | A | 7/1976 | Horn |
| 3,973,021 | A | 8/1976 | Horn |
| 3,974,277 | A | 8/1976 | Horn |
| 4,642,347 | A | 2/1987 | Kreft, III |
| 4,952,567 | A | 8/1990 | DeMeyts |
| 5,240,940 | A | 8/1993 | Arnold |
| 5,245,036 | A | 9/1993 | Robey |
| 5,324,839 | A | 6/1994 | Clemence |
| 5,436,233 | A | 7/1995 | Lee |
| 5,478,938 | A | 12/1995 | Clemence |
| 5,598,994 | A | 2/1997 | Olewinski |
| 5,817,674 | A | 10/1998 | Clemence |
| 5,840,695 | A | 11/1998 | Frank |
| 5,885,803 | A | 3/1999 | Bandman |
| 5,906,819 | A | 5/1999 | Kaibuchi |
| 5,932,470 | A | 8/1999 | Frank |
| 5,958,944 | A | 9/1999 | Arita |
| 5,972,598 | A | 10/1999 | Chaudhary |
| 5,977,102 | A | 11/1999 | Himmelsbach |
| 6,004,979 | A | 12/1999 | Clemence |
| 6,153,617 | A | 11/2000 | Bridges |
| 6,184,226 | B1 | 2/2001 | Chakravarty |
| 6,207,148 | B1 | 3/2001 | Bandman |
| 6,218,410 | B1 | 4/2001 | Uehata |
| 6,277,989 | B1 | 8/2001 | Chakravarty |
| 6,326,373 | B1 | 12/2001 | Uckun |
| 6,391,874 | B1 | 5/2002 | Cockerill |
| 6,794,389 | B2 | 9/2004 | Okana |
| 6,890,930 | B1 | 5/2005 | Mederski |
| 2001/0014679 | A1 | 8/2001 | Tang |
| 2001/0044442 | A1 | 11/2001 | Uckun |
| 2002/0025968 | A1 | 2/2002 | Pamukcu |
| 2002/0055514 | A1 | 5/2002 | Uckun |

FOREIGN PATENT DOCUMENTS

| DE | 2 135 172 | 5/1905 |
|---|---|---|
| DE | 2 140 280 | 2/1972 |
| EP | 1 163 910 | 12/2001 |
| EP | 1 174 150 | 1/2002 |
| EP | 1 034 793 | 2/2002 |
| EP | 1 177 796 | 2/2002 |

(Continued)

OTHER PUBLICATIONS

Vippagunta, S.R. et. al., "Crystalline solids", Advanced Drug Delivery Reviews, 2001, vol. 48, pp. 3-26.*

(Continued)

*Primary Examiner*—James O Wilson
*Assistant Examiner*—Tamthom N Truong

(57) ABSTRACT

Quinazolines of the formula I

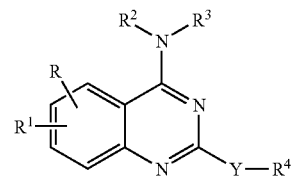

in which
R, $R^1$, $R^2$, $R^3$, $R^4$ and Y have the meaning indicated in Patent Claim 1, and their salts or solvates as glycoprotein IbIX antagonists.

3 Claims, No Drawings

FOREIGN PATENT DOCUMENTS

| WO | WO 95/28387 | 10/1995 |
|---|---|---|
| WO | WO 96/40142 | 12/1996 |
| WO | WO 97/03069 | 1/1997 |
| WO | WO 98/02438 | 1/1998 |
| WO | WO 99/09986 | 3/1999 |
| WO | WO 99/23113 | 5/1999 |
| WO | WO 99/24440 | 5/1999 |
| WO | WO 99/35132 | 7/1999 |
| WO | WO 99/35146 | 7/1999 |
| WO | WO 99/65908 | 12/1999 |
| WO | WO 00/12497 | 3/2000 |
| WO | WO 00/13497 | 3/2000 |
| WO | WO 00/57914 | 10/2000 |
| WO | WO 01/09134 | 2/2001 |
| WO | WO 02/24666 | 3/2002 |
| WO | WO 02/24667 | 3/2002 |
| WO | WO 02/30465 | 4/2002 |
| WO | WO 02/36577 | 5/2002 |
| WO | WO 02/53143 | 7/2002 |

OTHER PUBLICATIONS

Botros et al., Chemical Abstracts, 1988, vol. 109, Abstract #211005n.

Fadeeva et al., Chemical Abstracts, 1987, vol. 107, Abstract #70301a.

Foster et al.: "Pharmacological Rescue of Mutant P53 Conformation A. Function", Science, vol. 286, Dec. 24, 1999 pp. 2507-2510 XP000891848.

Lee et al. "Discovery of Potent Cyclic GMP Phosphodiesterase Inhibitors . . . " J. Med. Chem, 1995, vol. 38, No. 18, pp. 3547-3557.

Moshalenko et al., Chemical Abstracts, 1987, vol. 106, Abstract #32975v.

Zhikhareva et al., Chemical Abstracts, 1991, vol. 114, Abstract #95118d.

Zhikhareva et al., Chemical Abstracts, 1985, vol. 102, Abstract # 203929g.

Zhikhareva et al., Chemical Abstracts, 1983, vol. 98, Abstract #16639x.

Zhikhareva et al., Chemical Abstracts, 1982, vol. 96, Abstract #199625t.

Zhikhareva et al., Chemical Abstracts, 1980, vol. 93, Abstract #114434v.

Zhikhareva et al., Chemical Abstracts, 1980, vol. 93, Abstract #204585z.

* cited by examiner

4-AMINO-QUINAZOLINES

CROSS REFERENCE TO RELATED APPLICATIONS

This application is a continuation of U.S. Ser. No. 10/380,909, filed Mar. 20, 2003 now abandoned which is the national stage (371) filing of PCT/EP2001/10704, filed Sep. 17, 2001, which claims priority from U.S. Ser. No. 09/666,117, filed on Sep. 20, 2000. U.S. Ser. No. 09/666,117 was converted to provisional application Ser. No. 60/367,348. The entire disclosures of the above are hereby incorporated in their entirety.

FIELD OF THE INVENTION

The invention relates to substituted 4-amino-quinazolines of the formula I

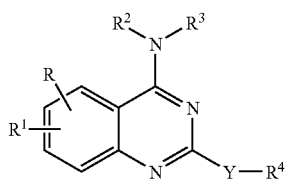

in which

R and $R^1$ are independently of each other H, A, $OR^5$, Hal, $N(R^5)_2$, $NO_2$, CN, $C(O)R^2$, $CON(R^5)_2$, $COOR^5$, allyl, CH=CH—$COOR^5$, CH=CHCON$(R^5)_2$, $SO_2A$ or phenyl, which is unsubstituted or mono-, di- or trisubstituted by A, $R^2$ and $R^3$ are independently of each other H, A, cycloalkyl, -$Het^3$, —$(CH_2)_o$—$OR^5$, —$(CH_2)_o$—$OR^6$, —$(CH_2)_o$-$Het^1$, —$(CH_2)_o$—$NR^5$-$Het^1$, —$(CHA)_p$-$(CH_2)_o$—$N(R^5)_2$, —$(CH_2)_p$—$(CHA)_p$-$(CH_2)_m$—Ar, —$(CH_2)_o$—Z—$(CH_2)_q$—$N(R^5)_2$,

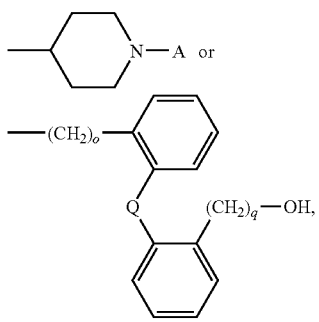

provided that $R^2$ and $R^3$ together are not H,
or $NR^2R^3$ together form a saturated monocyclic heterocyclic radical having to 6 ring members, where 1 or 2 N atoms are present and the heterocyclic radical can be mono- or disubstituted by OH, Ar, OAr or arylalkyl,
$R^4$ is Ar or $Het^1$,
$R^5$ is H or A,
$R^6$ is benzo[1,3]dioxol-5-yl,
Q is O or S,
Y is $(CH=CH)_n$,
Z is phenylene, cyclohexylene, —$NR^5$—, O, —CH(OH)—, —$CA_2$- or

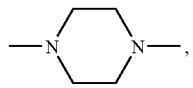

A is unbranched or branched alkyl having 1 to 6 carbon atoms,
Ar is phenyl, naphthyl or biphenyl, which is unsubstituted or mono-, di- or trisubstituted by A, $OR^5$, cycloalkyloxy, O—$(CH_2)_p$-Ph, $CF_3$, $OCF_3$, Hal, CN, CHO, COA, $COOR^5$, $N(R^5)_2$, $NR^5$—COA, $NO_2$, $SO_2N(R^5)_2$, mor, $SO_2$-mor, 5-methyl-3-oxo-2,4-dihydropyrazol-2-yl, naphthyl or $Het^2$,
$Het^1$ is a saturated, partially or completely unsaturated mono- or bicyclic heterocyclic radical having 5 to 10 ring members, where 1 or 2 N and/or 1 or 2 S or O atoms can be present and the heterocyclic radical can be mono- or disubstituted by A, Hal, $OR^5$, $CF_3$, $OCF_3$, $N(R^5)_2$, carbonyl oxygen, $COOR^5$, $Het^2$, benzyl or phenyl which is unsubstituted or mono-, di- or trisubstituted by A, $OR^5$, $CF_3$, $OCF_3$, Hal, CN, $COOR^5$, $N(R^5)_2$, $NO_2$ or $SO_2N(R^5)_2$,
$Het^2$ is a unsaturated mono- or bicyclic heterocyclic radical having 5 to 10 ring members, where 1 or 2 N and/or 1 or 2 S or O atoms can be present and the heterocyclic radical can be mono- or disubstituted by A, Hal, $OR^5$, $CF_3$, $OCF_3$, $N(R^5)_2$ or $COOR^5$,
$Het^3$ is a partially or completely unsaturated mono- or bicyclic heterocyclic radical having 5 to 10 ring members, where 1 or 2 N atoms are present and the heterocyclic radical can be mono- or disubstituted by A, Hal, $OR^5$, $CF_3$, $OCF_3$, $N(R^5)_2$, $SO_2A$ or $COOR^5$ provided that the heterocyclic radical is not bonded via an N atom,
Hal is F, Cl, Br or I,
mor is morpholin-4-yl,
Ph is phenyl,
n is 1 or 2,
m is 0, 1, 2, 3, 4, 5 or 6,
o is 1, 2, 3, 4, 5, 6 or 7,
p is 0, 1, 2, 3 or 4,
q is 1, 2, 3 or 4, and their pharmaceutically tolerable salts and solvates as glycoprotein IbIX antagonists.

Similar 4-amino substituted quinazolines are disclosed in WO 99/09986, Mastafanova, L I et al, Khim.-Farm. Zh. 1982, 16, 93842 or DE 2135172.

The invention is based on the object of finding novel glycoprotein IbIX inhibitors which can be used for the production of medicaments.

It has been found that the compounds of the formula I according to claims 1 to 5 and their salts or solvates act especially as GPIbIX inhibitors, in particular inhibiting the interaction of this receptor with the ligand von Willebrand factor (vWF). This action can be demonstrated, for example, by a method which is described by S. Meyer et al. in J. Biol. Chem. 1993, 268, 20555-20562. The property as GPIbIX alpha-thrombin receptor (N. J. Greco, Biochemistry 1996, 35, 915-921) can also be blocked by the compounds mentioned.

The significance of GPIbIX as an adhesion receptor on platelets, which mediates the primary interaction of platelets with an arteriosclerotically modified vascular wall via binding to the vWF expressed there, has been described by many authors (e.g. Z. M. Ruggeri in Thromb. Hemost. 1997, 78, 611-616). The activation of another platelet adhesion receptor, GPIIbIIIa, following the GPIbIX-vWF interaction, leads to platelet aggregation and thus to thrombotic vascular occlusion.

A GPIbIX antagonist can thus prevent the start of thrombus formation and thus also release of active substances from the platelets which, for example, promote thrombus growth and have an additional trophic action on the vascular wall. This has been shown with inhibitory peptides or antibodies in various experimental models (e.g. H Yamamoto et al., Thromb. Hemost. 1998, 79, 202-210).

In the case of higher shear forces, the blocking action of GPIbIX inhibitors exerts its maximum effect, as described by J. J. Sixma et al. in Arteriosclerosis, Thrombosis, and Vascular Biology 1996, 16, 64-71. According to the flow chamber method used there, the compounds of the formula I can be characterized as GPIbIX inhibitors in whole blood.

The inhibition of thrombus formation of the GPIbIX inhibitors can be measured by a modified Born method (Nature 1962, 4832, 927-929) using botrocetin or ristocetin as an aggregation stimulant.

The compounds of the formula I according to the invention can therefore be employed as pharmaceutical active compounds in human and veterinary medicine. They act as adhesion receptor antagonists, in particular as glycoprotein IbIX antagonists, and are suitable for the prophylaxis and/or therapy of thrombotic disorders and sequelae deriving therefrom. The preferentially best action is to be expected in the case of thrombotic disorders in the arterial vascular system, but GPIbIX inhibitors also have an effect in the case of thrombotic disorders in the venous vascular bed. The disorders are acute coronary syndromes, angina pectoris, myocardial infarct, peripheral circulatory disorders, stroke, transient ischaemic attacks, arteriosclerosis, reocclusion/restenosis after angioplasty/stent implantation. The compounds can furthermore be employed as anti-adhesive substances where the body comes into contact with foreign surfaces such as implants, catheters or cardiac pacemakers.

Comparison medication introduced onto the market which may be mentioned are aspirin and GPIIbIIIa antagonists.

The invention relates furthermore to novel compounds of the formula I and their salts or solvates, especially of compounds relating to group Ia to Ic, and to a process for the preparation of these novel compounds and their salts or solvates, characterized in that a) a compound of the formula I according to claims 1 to 4 is liberated from one of its functional derivatives by treating with a solvolysing or hydrogenolysing agent, or b) in stage 1) a compound of the formula II

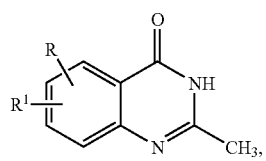

II in which
R and $R^1$ have the meaning as given in Claims 1 to 4, is reacted with a compound of the formula III

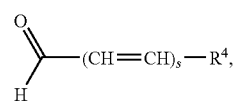

III in which $R^4$ has the meaning indicated in Claims 1 to 4 and s is 0 or 1, to give a compound of formula IV

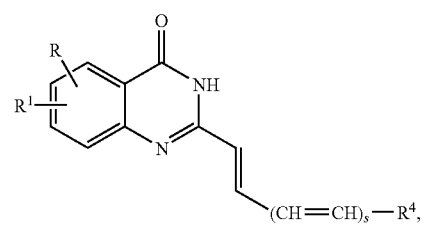

IV in which R, $R^1$ and $R^4$ have the meaning indicated in Claims 1 to 4 and s is 0 or 1, in stage 2) a compound of formula IV as indicated above is reacted with a chlorinating agent to give a compound of formula V

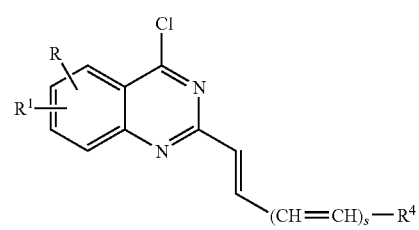

V in which R, $R^1$ and $R^4$ have the meaning indicated in Claims 1 to 4 and s is 0 or 1, and in stage 3) a compound of formula V as indicated above is reacted with a compound of formula VI

VI in which $R^2$ and $R^3$ or $NR^2R^3$ have the meaning indicated in Claims 1 to 4, or c) in stage 1) a compound of the formula II

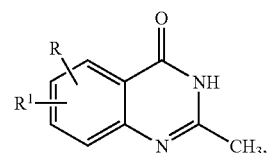

II in which

R and R¹ have the meaning as given in Claims 1 to 4, is reacted with a chlorinating agent to give a compound of formula VII

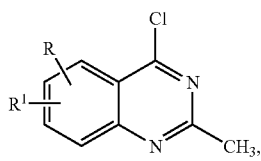

VII in which

R and R¹ have the meaning as given in Claims 1 to 4, in stage 2) a compound of formula VII as indicated above is reacted with a compound of formula VI

VI in which R² and R³ or NR²R³ have the meaning indicated in Claims 1 to 4 to give a compound of formula VIII

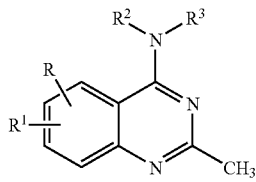

VIII in which R, R¹, R², R³ and NR²R³ have the meaning indicated in Claims 1 to 4 and in stage 3) a compound of formula VIII as indicated above is reacted with a compound of formula III

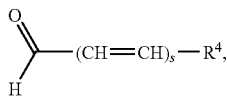

III in which R⁴ has the meaning indicated in Claims 1 to 4 and s is 0 or 1 or d) a radical R, R¹, R², R³ and/or R⁴ is converted into another radical R, R¹, R², R³ and/or R⁴ by, for example reducing a nitro group, sulfonyl group or sulfoxyl group;

etherifying an OH group or subjecting an OA group to ether cleavage, alkylating a primary or secondary amino group, partially or completely hydrolysing a CN group, cleaving an ester group or esterifying a carboxylic acid radical, reacting an aryl bromide, aryl iodide, heteroaryl bromide or heteroaryliodide to give the corresponding coupling products by means of a Suzuki coupling with boronic acids, reacting a iodoquinazoline or bromoquinazoline to give the corresponding coupling products by means of a Stille coupling with allyltributyltin, reacting a iodoquinazoline or bromoquinazoline to give the corresponding coupling products by means of a Heck coupling with acrylates, or carrying out a nucleophilic or electrophilic substitution, and/or a base or acid of the formula I is converted into one of its salts or solvates.

The compounds of the formula I can have a chiral center and therefore occur in a number of stereoisomeric forms. All these forms (e.g. R and S forms) and their mixtures (e.g. the RS forms) are included in the formula I.

The compounds according to the invention also include so-called prodrug derivatives, i.e. compounds of the formula I modified with, for example, alkyl or acyl groups, sugars or oligopeptides and which are rapidly cleaved in the body to give the active compounds according to the invention.

Furthermore, free amino groups as substituents of compounds of the formula I can be provided with appropriate conventional protective groups. CHO, COA, COOR⁵, N(R⁵)₂, NR⁵—COA, NO₂, SO₂N(R⁵)₂, mor, SO₂-mor, 5-methyl-3-oxo-2,4-dihydropyrazol-2-yl, naphthyl or Het².

Ar is preferentially phenyl, preferably—as indicated—mono- di- or trisubstituted phenyl, specifically preferentially phenyl, 2-, 3- or 4-methylphenyl, 2-, 3- or 4-ethylphenyl, 2-, 3- or 4-propylphenyl, 2-, 3- or 4-isopropylphenyl, 2-, 3- or 4-butylphenyl, 2-, 3- or 4-tert-butylphenyl, 2-, 3- or 4-aminophenyl, 2-, 3- or 4-N,N-dimethylaminophenyl, 2-, 3- or 4-sulfamoylphenyl, 2-, 3- or 4-nitrophenyl, 2-, 3- or 4-hydroxyphenyl, 2-, 3- or 4-methoxyphenyl, 2-, 3- or 4-ethoxyphenyl, 2-, 3- or 4-pentoxyphenyl, 2-, 3- or 4-phenoxyphenyl, 2-, 3- or 4-phenylmethoxyphenyl, 2-, 3- or 4-trifluoromethylphenyl, 2-, 3- or 4-trifluoromethoxyphenyl, 2-, 3- or 4-cyclopentyloxyphenyl, 2-, 3- or 4-carboxyphenyl, 2-, 3- or 4-(N,N-diethyl)sulfamoylphenyl, 2-, 3- or 4-cyanophenyl, 2-, 3- or 4-fluorophenyl, 2-, 3- or 4-chlorophenyl, 2-, 3- or 4-bromophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3-, 2,4-, 2,5-, 2,6-, 3,4- or 3,5-dimethoxyphenyl, 2,3-, 2,4-, 2,5-, 2,6-, 3,4- or 3,5-di(trifluoromethyl)phenyl, 2,3-, 2,4-, 2,5-, 2,6-, 3,4- or 3,5-di(phenylmethoxy)phenyl, 2-chloro-6-methylphenyl, 2-chloro-4-fluorophenyl, 3-bromo-6-fluorophenyl, 3,4,5-trimethoxyphenyl, 4-(morpholin-4-yl)phenyl, 4-(morpholin-4-yl-sulfonyl)phenyl, 4-(5-methyl-3-oxo-2,4-dihydropyrazol-2-yl)phenyl, 4-(4,6-dimethoxy-pyrimidin-2-yl)phenyl, 3-(4,6-dimethoxy-pyrimidin-2-yl)phenyl, 4-(pyrid-3-yl)phenyl, 3-(pyrid-3-yl)phenyl, 4-(thiophen-2-yl)phenyl, 3-(thiophen-2-yl)phenyl, 4-(benzo[c]thiophen-2-yl)phenyl or 4-(naphthalen-1-yl)phenyl.

Furthermore, however, Ar is also preferentially unsubstituted naphthyl or biphenyl—as indicated—or alternatively mono-, di- or trisubstituted biphenyl, specifically preferentially biphenyl-4-yl or biphenyl-3-yl, 2'-methylbiphenyl-4-yl, 3'-methylbiphenyl-4-yl, 4'-methylbiphenyl-4-yl, 2'-methylbiphenyl-3-yl, 3'-methylbiphenyl-3-yl, 4'-methylbiphenyl-3-yl, 2-methylbiphenyl-4-yl, 3-methylbiphenyl-4-yl, 2-methylbiphenyl-3-yl, 4-methylbiphenyl-3-yl, 2'-tert-butylbiphenyl-4-yl, 3'-tert-butylbiphenyl-4-yl, 4'-tert-butylbiphenyl-4-yl, 2'-tert-butylbiphenyl-3-yl, 3'-tert-butylbiphenyl-3-yl, 4'-tert-butylbiphenyl-3-yl, 2-tert-butylbiphenyl-4-yl, 3-tert-butylbiphenyl-4-yl, 2-tertbutylbiphenyl-3-yl, 4-tert-butylbiphenyl-3-yl, 2'-isopropylbiphenyl-4-yl, 3'-isopropylbiphenyl-4-yl, 4'-isopropylbiphenyl-4-yl, 2'-isopropylbiphenyl-3-yl, 3'-isopropylbiphenyl-3-yl, 4'-isopropylbiphenyl-3-yl, 2-isopropylbiphenyl-4-yl, 3-isopropylbiphenyl-4-yl, 2-isopropylbiphenyl), 4-isopropylbiphenyl-3-yl, 2'-fluorobiphenyl-4-yl, 3'-fluorobiphenyl-4-yl, 4'-fluorobiphenyl-4-yl, 2'-fluorobiphenyl-3-yl, 3'-fluorobiphenyl-3-yl, 4'-fluorobiphenyl-3-yl, 2-fluorobiphenyl-4-yl, 3-fluorobiphenyl-4-yl, 2-fluorobiphenyl-3-yl, 4-fluorobiphenyl-3-yl, 2'-chlorobiphenyl-4-yl, 3'-chlorobiphenyl-4-yl, 4'-chlorobiphenyl-4-yl, 2'-chlorobiphenyl-3-yl, 3'-chlorobiphenyl-3-yl, 4'-chlorobiphenyl-3-yl, 2-chlorobiphenyl-4-yl, 3-chlorobiphenyl-4-yl 2-chlorobiphenyl-3-yl, 4-chlorobiphenyl-3-yl, 2'-methoxybiphenyl-4-yl, 3'-methoxybiphenyl-4-yl, 4'-methoxybiphenyl-4-yl, 2'-methoxybiphenyl-3-yl, 3'-methoxybiphenyl-3-yl, 4'-methoxybiphenyl-3-yl, 2-methoxybiphenyl-4-yl, 3-methoxybiphenyl-4-yl, 2-methoxybiphenyl-3-yl, 4-methoxybiphenyl-3-yl, 2'-nitrobiphenyl-4-yl, 3'-nitrobiphenyl-4-yl, 4'-nitrobiphenyl-4-yl, 2'-nitrobiphenyl-3-yl, 3'-nitrobiphenyl-3-yl, 4'-nitrobiphenyl-3-yl, 2-nitrobiphenyl-4-yl, 3-nitrobiphenyl-4-yl, 2-nitrobiphenyl-3-yl, 4-nitrobiphenyl-3-yl, 2'-trifluoromethylbiphenyl-4-yl, 3'-trifluoromethylbiphenyl-4-yl, 4'-trifluoromethyl-biphenyl-4-yl, 2'-trifluoromethylbiphenyl-3-yl, 3'-trifluoromethylbiphenyl-3-yl, 4'-trifluoromethylbiphenyl-3-yl, 2-trifluoromethylbiphenyl-4-yl, 3-trifluoromethylbiphenyl-4-yl, 2-trifluoromethylbiphenyl-3-yl, 4-trifluoromethylbiphenyl-3-yl, 2'-trifluoromethoxybiphenyl-4-yl, 3'-trifluoromethoxybiphenyl-4-yl, 4'-trifluoromethoxybiphenyl-4-yl, 2'-trifluoromethoxybiphenyl-3-yl, 3'-trifluoromethoxybiphenyl-3-yl, 4'-trifluoromethoxybiphenyl-3-yl, 2-trifluoromethoxybiphenyl-4-yl, 3-trifluoromethoxybiphenyl-4-yl, 2-trifluoromethoxybiphenyl-3-yl, 4-trifluoromethoxybiphenyl-3-yl, 3'-acetylbiphenyl-4-yl, 3'-acetylaminobiphenyl-4-yl, 3'-aminobiphenyl-4-yl, furthermore preferentially disubstituted biphenyls, such as 2'-methyl-3'-nitrobiphenyl-4-yl, 2'-methyl-4'-nitrobiphenyl-4-yl, 2'-methyl-5'-nitrobiphenyl-4-yl, 2'-methyl-6'-nitrobiphenyl-4-yl, 3'-methyl-2'-nitrobiphenyl-4-yl, 3'-methyl-4'-nitrobiphenyl-4-yl, 3'-methyl-5'-nitrobiphenyl-4-yl, 3'-methyl-6'-nitrobiphenyl-4-yl, 4'-methyl-2'-nitrobiphenyl-4-yl, 4'-methyl-3'-nitrobiphenyl-4-yl, 2'-methyl-3'-nitrobiphenyl-3-yl, 2'-methyl-4'-nitrobiphenyl-3-yl, 2'-methyl-5'-nitrobiphenyl-3-yl, 2'-methyl-6'-nitrobiphenyl-3-yl, 3'-methyl-2'-nitrobiphenyl-3-yl, 3'-methyl-4'-nitrobiphenyl-3-yl, 3'-methyl-5'-nitrobiphenyl-3-yl, 3'-methyl-6'-nitrobiphenyl-3-yl, 4'-methyl-2'-nitrobiphenyl-3-yl, 4'-methyl-3'-nitrobiphenyl-3-yl, 2'-methoxy-2-methylbiphenyl-4-yl, 3'-methoxy-2-methylbiphenyl-4-yl, 4'-methoxy-2-methylbiphenyl-4-yl, 4'-methoxy-3-nitrobiphenyl-4-yl, 2'-chloro-3'-fluorobiphenyl-4-yl, 2'-chloro-4'-fluorobiphenyl-4-yl, 2'-chloro-5'-fluorobiphenyl-4-yl, 2'-chloro-6'-fluorobiphenyl-4-yl, 3'-chloro-2'-fluorobiphenyl-4-yl, 3'-chloro-4'-fluorobiphenyl-4-yl, 3'-chloro-5'-fluorobiphenyl-4-yl, 3'-chloro-6'-fluorobiphenyl-4-yl, 4'-chloro-2'-fluorobiphenyl-4-yl, 4'-chloro-3'-fluorobiphenyl-4-yl, 2'-chloro-3'-fluorobiphenyl-3-yl, 2'-chloro-4'-fluorobiphenyl-3-yl, 2'-chloro-5'-fluorobiphenyl-3-yl, 2'-chloro-6'-fluorobiphenyl-3-yl, 3'-chloro-2'-fluorobiphenyl-3-yl, 3'-chloro-4'-fluorobiphenyl-3-yl, 3'-chloro-5'-fluorobiphenyl-3-yl, 3'-chloro-6'-fluorobiphenyl-3-yl, 4'-chloro-2'-fluorobiphenyl-3-yl, 4'-chloro-3'-fluorobiphenyl-3-yl, (2,3'-diethyl)biphenyl-4-yl, (3,3'-diethyl)biphenyl-4-yl), (2,2'-diethyl)biphenyl-4-yl, (2,4'-diethyl)biphenyl-4-yl, (2',3'-dimethoxy)biphenyl-4-yl, (2',4'-dimethoxy)biphenyl-4-yl, (2',5'-dimethoxy)biphenyl-4-yl, (2',6'-dimethoxy)-biphenyl-4-yl, (3',4'-dimethoxy)biphenyl-4-yl, (3',5'-dimethoxy)biphenyl-4-yl, (2',3'-dimethoxy)-biphenyl-3-yl, (2',4'-dimethoxy)biphenyl-3-yl, (2',5'-dimethoxy)biphenyl-3-yl, (2',6'-dimethoxy)-biphenyl-3-yl, (3',4'-dimethoxy)biphenyl)-3-yl, (3',5'-dimethoxy)biphenyl-3-yl, (3',5'-dichloro)biphenyl-4-yl, (3',5'-dichloro)biphenyl-3-yl, (2',4'-dichloro)biphenyl-4-yl, (3',4',5'-trimethoxy)biphenyl-4-yl, (2',3'-di(trifluoromethyl))biphenyl-4-yl, (2',4'-di(trifluoromethyl))biphenyl-4-yl, (2',5'-di(trifluoromethyl)) biphenyl-4-yl, (2',6'-di(trifluoromethyl))biphenyl-4-yl, (3', 4'-di(trifluoromethyl))biphenyl-4-yl, (3',5'-di (trifluoromethyl))biphenyl-4-yl, (2',3'-di(trifluoromethyl)) biphenyl-3-yl, (2',4'-di(trifluoromethyl))biphenyl-3-yl, (2', 5'-di(trifluoromethyl))biphenyl-3-yl, (2',6'-di (trifluoromethyl))biphenyl-3-yl, (3',4'-di(trifluoromethyl)) biphenyl-3-yl, (3',5'-di(trifluoromethyl)biphenyl-3-yl, (2,2'-dimethyl)biphenyl-4-yl, (2,'3-dimethyl)biphenyl-4-yl, (2,4'-dimethyl)biphenyl-4-yl, (2,2'-dimethyl)biphenyl-3-yl, (2,3'-dimethyl)biphenyl-3-yl or (2,4'-dimethyl)biphenyl-3-yl.

Phenyl, 2-, 3- or 4-fluorophenyl, 3- or 4-chlorophenyl, 4-bromophenyl, 2,4- or 3,4-dichlorophenyl, 2,3-dimethoxyphenyl, 4-aminophenyl, 4-dimethylaminophenyl, 2-, 3- or 4-methylphenyl, 2-, 3- or 4-methoxyphenyl, 4-propylphenyl, 4-isopropylphenyl, 4-butylphenyl, 2-, 3- or 4-nitrophenyl, 2-, 3- or 4-pentoxyphenyl, 2-, 3- or 4-phenoxyphenyl, 2-, or 4-phenylmethoxyphenyl, 2-, 3- or 4-trifluoromethylphenyl, 2-, 3- or 4-trifluoromethoxyphenyl, 2- or 4-cyclopentyloxyphenyl, 3- or 4-carboxyphenyl, 2-, 3- or 4-(N,N-diethyl) sulfamoylphenyl, 3,4-di(phenylmethoxy)phenyl, 2-chloro-6-methylphenyl, 2-chloro-4-fluorophenyl, 5-bromo-2-fluorophenyl, 3,4,5-trimethoxyphenyl, 4-(morpholin-4-yl) phenyl, 4-(morpholin-4-yl-sulfonyl)phenyl, 4-(5-methyl-3-oxo-2,4-dihydropyrazol-2-yl)phenyl, 4-(4,6-dimethoxypyrimidin-2-yl)phenyl, 3-(4,6-dimethoxy-pyrimidin-2-yl) phenyl, 4-(pyrid-3-yl)phenyl, 3-(pyrid-3-yl)phenyl, 4-(thiophen-2-yl)phenyl, 3-(thiophen-2-yl)phenyl, 4-(benzo[c]thiophen-2-yl)phenyl, 4-(naphthalen-1-yl)phenyl, naphthyl, biphenyl-4-yl, 2'-fluorobiphenyl-4-yl, 4'-fluorobiphenyl-4-yl, 4'-fluorobiphenyl-3-yl, 4'-chlorobiphenyl-4-yl, 4'-chlorobiphenyl-3-yl, 4'-methoxybiphenyl-4-yl, 4'-methoxybiphenyl-3-yl, 3'-nitrobiphenyl-4-yl, 3'-acetylbiphenyl-4-yl, 3'-acetylaminobiphenyl-4-yl, 3'-aminobiphenyl-4-yl, (2,3'-diethyl)biphenyl-4-yl, (3',5'-dichloro)biphenyl-3-yl, (2',4'-dichloro)biphenyl-4-yl, (3',4',5'-trimethoxy)biphenyl-4-yl, (3',5'-di(trifluoromethyl))biphenyl-4-yl, is particularly preferred for Ar.

Arylalkyl is preferentially benzyl.

O—$(CH_2)_p$-Ph is phenylalkyloxy, in which p can be 0, 1, 2, 3 or 4. Benzyloxy or phenyloxy is particularly preferred.

Cycloalkyl preferably has 3-7 C atoms and is preferably cyclopropyl, cyclobutyl, cyclopentyl or cyclohexyl, and further also cyclopentylmethyl, cyclopentylethyl or cyclohexylmethyl; cyclopentyl, cyclohexylmethyl or cyclohexyl are particularly preferred.

Hal is preferably F, Cl, Br or I.

$Het^1$ is a saturated, partially or completely unsaturated mono- or bicyclic heterocyclic radical having 5 to 10 ring members, where 1 or 2 N and/or 1 or 2 S or O atoms can be present and the heterocyclic radical can be mono- or disubstituted by A, Hal, $OR^5$, $CF_3$, $OCF_3$, $N(R^5)_2$, carbonyl oxygen, $COOR^5$, $Het^2$, benzyl or phenyl which is unsubstituted or mono-, di- or trisubstituted by A, $OR^5$, $CF_3$, $OCF_3$, Hal, CN, $COOR^5$, $N(R^5)_2$, $NO_2$, $SO_2N(R^5)_2$.

$Het^1$ is preferably unsubstituted 2- or 3-furyl, 2- or 3-thiophenyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -4- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H- thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothiophenyl, 1-, 2-, 3-, 4-, 5-, 6- or 7-1H-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 1-, 2-, 3-, 4-, 5-, 6-, 7- or 8-quinolinyl, 1-, 3-, 4-, 5-, 6-, 7- or 8-isoquinolinyl, 1-, 2-, 3-, 4- or 9-carbazolyl, 1-, 2-, 3-, 4-, 5-, 6-, 7-, 8- or 9-acridinyl, 3-, 4-, 5-, 6-, 7- or 8-cinnolinyl, 2-, 4-, 5-, 6-, 7- or 8-quinazolinyl. The heterocyclic radicals can also be partially or completely hydrogenated. Het can thus also be 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2 or -3-thiophenyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -3-pyrrolyl, tetrahydro-1-, -2- or 4-imidazolyl, 2,3-dihydro-1-, -2-, -3-, -4-, -5-, -6-, -7-1H-indolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1,2,3,6-tetrahydro-1-, -2-, -3-, -4-, -5- or -6-pyridyl, 1-, 2-, 3- or 4-piperidinyl, 1-, 2-, 3- or 4-azepanyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or 4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolinyl, 1,2,3,4-tetrahydro-1-, -2-, -3-, -4-, -5-, -6-, -7- or -8-isoquinolinyl which can be substituted as indicated above or particularly substituted by A, OA, carbonyl oxygen, NO$_2$, Het$^2$ or phenyl which is substituted by Hal, CN or OA.

Thiophen-2-yl, tetrahydro-furan-2-yl, 1-methyl-octahydro-indol-3-yl, benzo[1,3]dioxol-5-yl, piperazin-1-yl, 4-methyl-piperazin-1-yl, piperidin-1-yl, piperidin-4-yl, 4-benzyl-piperidin-1-yl, 2-methyl-piperidin-1-yl, 1-ethyl-pyrrolidin-2-yl, 1-methyl-pyrrolidin-2-yl, 2-oxo-pyrrolidin-1-yl, pyridin-2-yl, pyridin-4-yl, 5-nitro-pyridin-2-yl, imidazol-1-yl, morpholin-4-yl, 5-methoxy-1H-indol-2-yl, 5-(3-chlorophenyl)-furan-2-yl, 5-(4-fluorophenyl)-thiophen-2-yl, 5-(2-methoxyphenyl)-thiophen-2-yl, 5-(2-cyanophenyl)-thiophen-2-yl, 5-(2,5-dimethoxyphenyl)-thiophen-2-yl, 2-[2,2']bithiophenyl-5-yl, 5-(pyridin-4-yl)-thiophen-2-yl, 5-(1H-indol-5-yl)-thiophen-2-yl, 5-quinolin-8-yl-thiophen-2-yl or 5-(benzo[b]thiophen-2-yl)-thiophen-2-yl is particularly preferred for Het$^1$.

Het$^2$ is a unsaturated mono- or bicyclic heterocyclic radical having 5 to 10 ring members, where 1 or 2 N and/or 1 or 2 S or O atoms can be present and the heterocyclic radical can be mono- or disubstituted by A, Hal, OR$^5$, CF$_3$, OCF$_3$, N(R$^5$)$_2$ or COOR$^5$.

Thiophen-2-yl, pyridin-3-yl, pyridin-2-yl, pyridin-4-yl, indol-5-yl, quinolin-8-yl, 4,6-dimethoxy-pyrimidin-2-yl or benzo[b]thiophen-2-yl is particularly preferred for Het$^2$.

Het$^3$ is a partially or completely unsaturated mono- or bicyclic heterocyclic radical having 5 to 10 ring members, where 1 or 2 N atoms are present and the heterocyclic radical can be mono- or disubstituted by A, Hal, OR$^5$, CF$_3$, OCF$_3$, N(R$^5$)$_2$, SO$_2$A or COOR$^5$ provided that the heterocyclic radical is not bonded via an N atom.

Quinolin-5-yl and 1-methanesulfonyl-2,3-dihydro-1H-indol-5-yl is particularly preferred for Het$^3$.

(CH$_2$)$_o$—OR$^5$ is preferentially (CH$_2$)$_2$—OCH$_3$, (CH$_2$)$_3$—OCH$_3$ or (CH$_2$)$_3$—O(iPr). (CH$_2$)$_o$—OR$^6$ is preferentially

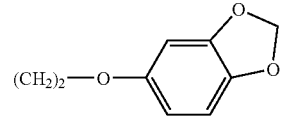

R and R$^1$ are independently of each other H, A, OR$^5$, Hal, N(R$^5$)$_2$, NO$_2$, CN, C(O)R$^2$, CON(R$^5$)$_2$, COOR$^5$, allyl, CH═CH—COOR$^5$, CH═CHCON(R$^5$)$_2$, SO$_2$A or phenyl, which is unsubstituted or mono-, di- or trisubstituted by A, where A and Hal have a preferred meaning indicated beforehand and R$^5$ have a preferred meaning indicated in the following.

R is preferentially H.

R$^1$ is preferentially H, Hal, allyl, CH═CH—COOR$^5$, CH═CHCON(R$^5$)$_2$ or phenyl, which is unsubstituted or monosubstituted by A, H, Cl, Br, I, CH═CH—COOEt, 4-methylphenyl, allyl or CH═CH—CONMe$_2$ is particularly preferred for R$^1$.

The preferred position of R$^1$ is the 6- or 7-position of the quinazoline ring system.

R$^2$ and R$^3$ are independently of each other H, A, cycloalkyl, -Het$^3$, —(CH$_2$)$_o$—OR$^5$, —(CH$_2$)$_o$—OR$^6$, —(CH$_2$)$_o$-Het$^1$, —(CH$_2$)$_o$—NR$^5$-Het$^1$, —(CHA)$_p$-(CH$_2$)$_o$—N(R$^5$)$_2$, —(CH$_2$)$_p$—(CHA)$_p$-(CH$_2$)$_m$—Ar, —(CH$_2$)$_o$—Z—(CH$_2$)$_q$—N(R$^5$)$_2$,

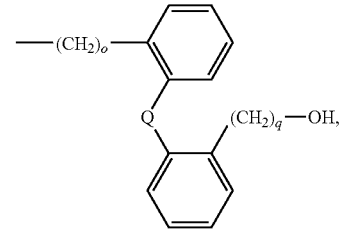

provided that R$^2$ and R$^3$ together are not H, where A, Ar, cycloalkyl, Het$^1$ or Het$^3$ have a preferred meaning indicated beforehand and R$^5$, R$^6$, Q and Z have a preferred meaning indicated in the following.

R$^2$ is preferentially H or A.

R$^3$ is preferentially A, cycloalkyl, -Het$^3$, —(CH$_2$)$_o$—OR$^5$, —(CH$_2$)$_o$—OR$^6$, —(CH$_2$)$_o$-Het$^1$, —(CH$_2$)$_o$—NR$^5$-Het$^1$, —(CHA)$_p$-(CH$_2$)$_o$—N(R$^5$)$_2$, —(CH$_2$)$_p$—(CHA)$_p$-(CH$_2$)$_m$—Ar, —(CH$_2$)$_o$—Z—(CH$_2$)$_q$—N(R$^5$)$_2$,

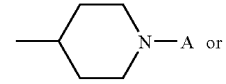

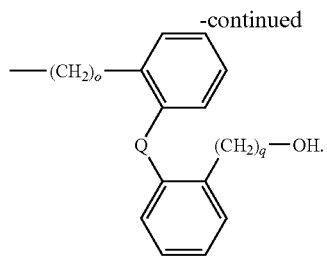

Furthermore NR²R³ together form a saturated monocyclic heterocyclic radical having 5 to 6 ring members, where 1 or 2 N atoms are present and the heterocyclic radical can be mono- or disubstituted by OH, Ar, OAr or arylalkyl, where Ar or arylalkyl have a preferred meaning indicated beforehand.

Preferred saturated monocyclic heterocyclic radicals can be piperidine or piperazine.

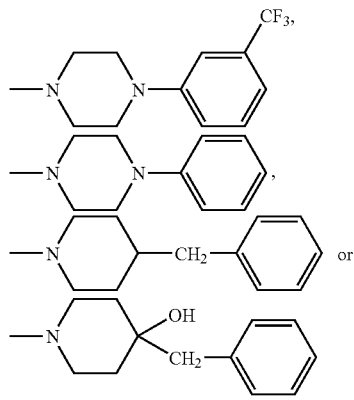

are particularly preferred for NR²R³.

R⁴ is Ar or Het¹, where Ar or Het¹ have a preferred meaning indicated beforehand.

R⁵ is H or A, where A has a preferred meaning indicated beforehand.

Q is O or S, preferentially O.

Y is (CH=CH)$_n$, where n can be 1 or 2.

Z is phenylene, cyclohexylene, —NR⁵—, O, —CH(OH)—, —CA₂- or

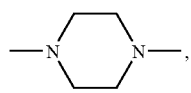

where R⁵ and A have a preferred meaning indicated beforehand. Phenylene and/or cyclohexylene are particularly bonded in 1,4- or 1,3-position.

m is 0, 1, 2, 3, 4, 5 or 6, preferentially 0, 1 or 2.

o is 1, 2, 3, 4, 5, 6 or 7, preferentially 1, 2, 3 or 7.

p is 0, 1, 2, 3 or 4, preferentially 0, 1 or 2.

q is 1, 2, 3 or 4, preferentially 1, 2 or 3.

Some preferred groups of compounds of formula I which are novel can be expressed by the following groups or sub-formulae Ia to Ic, which correspond to the formula I and in which the radicals not designated in greater detail have the meaning indicated in formula I according to Claim 1, but I. for the group Ia in which in Ia-1

R and R¹ are independently of each other H, A, OR⁵, Hal, N(R⁵)₂, NO₂, CN, C(O)R², CON(R⁵)₂, COOR⁵, allyl, CH=CH—COOR⁵, CH=CHCON(R⁵)₂, SO₂A or phenyl, which is unsubstituted or mono-, di- or trisubstituted by A, R² is H, R³ is —(CH₂)$_o$—Z—(CH₂)$_q$—N(R⁵)₂, R⁴ is Ar, R⁵ is H or A, Y is (CH=CH)$_n$, Z is phenylene, cyclohexylene, —NR⁵—, O, —CH(OH)—, —CA₂- or

A is unbranched or branched alkyl having 1 to 6 carbon atoms,

Ar is phenyl or naphthyl, which is unsubstituted or mono-, di- or trisubstituted by A, OR⁵, CF₃, OCF₃, Hal, CN, CHO, COA, COOR⁵, N(R⁵)₂, NO₂ or SO₂N(R⁵)₂, Hal is F, Cl, Br or I, n is 1 or 2, o is 1, 2, 3, 4, 5, 6 or 7 and q is 1, 2, 3 or 4;

in Ia-2

R and R¹ are independently of each other H or Hal,

R² is H,

R³ is —(CH₂)$_o$—Z—(CH₂)$_q$—N(R⁵)₂,

R⁴ is Ar,

R⁵ is H or A,

Y is (CH=CH)$_n$,

Z is phenylene, cyclohexylene, —NR⁵—, O, —CH(OH)—, —CA₂- or

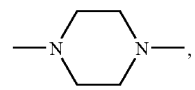

A is unbranched or branched alkyl having 1 to 6 carbon atoms,

Ar is phenyl or naphthyl, which is unsubstituted or mono-, di- or trisubstituted by A, OR⁵, Hal, COOR⁵, N(R⁵)₂ or NO₂, Hal is F, Cl, Br or I, n is 1 or 2, o is 1, 2 or 3 and q is 1, 2 or 3;

in Ia-3

R and R¹ are independently of each other H or Hal,

R² is H,

R³ is

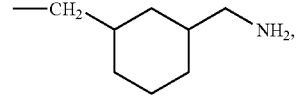

$R^4$ is Ar,
$R^5$ is H or A,
Y is $(CH=CH)_n$,
A is unbranched or branched alkyl having 1 to 6 carbon atoms,
Ar is phenyl or naphthyl, which is unsubstituted or mono-, di- or trisubstituted by A, $OR^5$, Hal, $COOR^5$, $N(R^5)_2$ or $NO_2$,
Hal is F, Cl, Br or I and
n is 1 or 2;

II. for the group Ib in which in Ib-1
R and $R^1$ are independently of each other H, A, $OR^5$, Hal, $N(R^5)_2$, $NO_2$, CN, $C(O)R^2$, $CON(R^5)_2$, $COOR^5$, allyl, $CH=CH-COOR^5$, $CH=CHCON(R^5)_2$, $SO_2A$ or phenyl, which is unsubstituted or mono-, di- or trisubstituted by A,
$R^2$ and $R^3$ are independently of each other H, A, cycloalkyl, -$Het^3$, $-(CH_2)_o-OR^5$, $-(CH_2)_o-OR^6$, $-(CH_2)_o-Het^1$, $-(CH_2)_o-NR^5-Het^1$, $-(CHA)_p-(CH_2)_o-N(R^5)_2$, $-(CH_2)_p-(CHA)_p-(CH_2)_m-Ar$ or $-(CH_2)_o-Z-(CH_2)_q-N(R^5)_2$,
provided that $R^2$ and $R^3$ together are not H,
$R^4$ is Ar,
$R^5$ is H or A,
$R^6$ is benzo[1,3]dioxol-5-yl,
Y is $(CH=CH)_n$,
Z is phenylene, cyclohexylene, $-NR^5-$, O, $-CH(OH)-$, $-CA_2-$ or

A is unbranched or branched alkyl having 1 to 6 carbon atoms,
Ar is phenyl, which is mono-, di- or trisubstituted by $O-(CH_2)_p-Ph$, naphthyl or $Het^2$, or biphenyl, which is unsubstituted or mono-, di- or trisubstituted by A, $OR^5$, $CF_3$, $OCF_3$, Hal, CN, CHO, COA, $COOR^5$, $N(R^5)_2$, $NR^5-COA$, $NO_2$, $SO_2N(R^5)_2$, naphthyl or $Het^2$,
$Het^1$ is a saturated, partially or completely unsaturated mono- or bicyclic heterocyclic radical having 5 to 10 ring members, where 1 or 2 N and/or 1 or 2 S or O atoms can be present and the heterocyclic radical can be mono- or disubstituted by A, Hal, $OR^5$, $CF_3$, $OCF_3$, $N(R^5)_2$, carbonyl oxygen, $COOR^5$, $Het^2$, benzyl or phenyl which is unsubstituted or mono-, di- or trisubstituted by A, $OR^5$, $CF_3$, $OCF_3$, Hal, CN, $COOR^5$, $N(R^5)_2$, $NO_2$ or $SO_2N(R^5)_2$,
$Het^2$ is a unsaturated mono- or bicyclic heterocyclic radical having 5 to 10 ring members, where 1 or 2 N and/or 1 or, 2 S or O atoms can be present and the heterocyclic radical can be mono- or disubstituted by A, Hal, $OR^5$, $CF_3$, $OCF_3$, $N(R^5)_2$ or $COOR^5$,
$Het^3$ is a partially or completely unsaturated mono- or bicyclic heterocyclic radical having 5 to 10 ring members, where 1 or 2 N atoms are present and the heterocyclic radical can be mono- or disubstituted by A, Hal, $OR^5$, $CF_3$, $OCF_3$, $N(R^5)_2$, $SO_2A$ or $COOR^5$ provided that the heterocyclic radical is not bonded via an N atom,
Hal is F, Cl, Br or I,
Ph is phenyl,
n is 1 or 2,
m is 0, 1, 2, 3, 4, 5 or 6,
o is 1, 2, 3, 4, 5, 6 or 7,
p is 0, 1, 2, 3 or 4 and
q is 1, 2, 3 or 4;

in which in Ib-2
R and $R^1$ are independently of each other H, Hal, allyl, $CH=CH-COOR^5$, $CH=CHCON(R^5)_2$ or phenyl, which is unsubstituted or mono-, di- or trisubstituted by A,
$R^2$ and $R^3$ are independently of each other H, cycloalkyl, $-(CH_2)_o-Het^1$, $-(CHA)_p-(CH_2)_o-N(R^5)_2$, $-(CH_2)_p-(CHA)_p-(CH_2)_m-Ar$ or $-(CH_2)_o-Z-(CH_2)_q-N(R^5)_2$,
provided that $R^2$ and $R^3$ together are not H,
$R^4$ is Ar,
$R^5$ is H or A,
Y is $(CH=CH)_n$,
Z is phenylene, cyclohexylene, $-NR^5-$, O, $-CH(OH)-$, $-CA_2-$ or

A is unbranched or branched alkyl having 1 to 6 carbon atoms,
Ar is phenyl, which is mono-, di- or trisubstituted by $O-(CH_2)_p-Ph$, naphthyl or $Het^2$, or biphenyl, which is unsubstituted or mono-, di- or trisubstituted by A, $OR^5$, $CF_3$, $OCF_3$, Hal, CN, CHO, COA, $COOR^5$, $N(R^5)_2$, $NR^5-COA$, $NO_2$, $SO_2N(R^5)_2$, naphthyl or $Het^2$,
$Het^1$ is a saturated, partially or completely unsaturated mono- or bicyclic heterocyclic radical having 5 to 10 ring members, where 1 or 2 N and/or 1 or 2 S or O atoms can be present and the heterocyclic radical can be mono- or disubstituted by A, Hal, $OR^5$, $CF_3$, $OCF_3$, $N(R^5)_2$, carbonyl oxygen, $COOR^5$, $Het^2$, benzyl or phenyl which is unsubstituted or mono-, di- or trisubstituted by A, $OR^5$, $CF_3$, $OCF_3$, Hal, CN, $COOR^5$, $N(R^5)_2$, $NO_2$ or $SO_2N(R^5)_2$,
$Het^2$ is a unsaturated mono- or bicyclic heterocyclic radical having 5 to 10 ring members, where 1 or 2 N and/or 1 or 2 S or O atoms can be present and the heterocyclic radical can be mono- or disubstituted by A, Hal, $OR^5$, $CF_3$, $OCF_3$, $N(R^5)_2$ or $COOR^5$,
Hal is F, Cl, Br or I,
Ph is phenyl,
n is 1 or 2,
m is 0, 1 or 2,
o is 1, 2, 3 or 7,
p is 0 or 1 and
q is 1, 2 or 3;

in which in Ib-3
R and $R^1$ are independently of each other H, Hal, allyl, $CH=CH-COOR^5$, $CH=CHCON(R^5)_2$ or phenyl, which is unsubstituted or mono-, di- or trisubstituted by A,
$R^2$ and $R^3$ are independently of each other H, cycloalkyl, $-(CH_2)_o-Het^1$, $-(CHA)_p-(CH_2)_o-N(R^5)_2$, $-(CH_2)_p-(CHA)_p-(CH_2)_m-Ar$ or $-(CH_2)_o-Z-(CH_2)_q-N(R^5)_2$,
provided that $R^2$ and $R^3$ together are not H,
$R^4$ is Ar,
$R^5$ is H or A,
Y is $(CH=CH)_n$,
Z is phenylene, cyclohexylene, $-NR^5-$, O, $-CH(OH)-$, $-CA_2-$ or

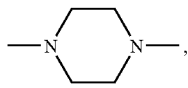

A is unbranched or branched alkyl having 1 to 6 carbon atoms,
Ar is phenyl, which is mono-, di- or trisubstituted by O—(CH$_2$)$_p$-Ph, naphthyl or Het$^2$, or biphenyl, which is unsubstituted or mono-, di- or trisubstituted by A, OR$^5$, CF$_3$, Hal, COA, N(R$^5$)$_2$, NO$_2$, NR$^5$—COA or Het$^2$,
Het$^1$ is thiophen-2-yl, tetrahydro-furan-2-yl, 1-methyl-octahydro-indol-3-yl, benzo[1,3]dioxol-5-yl, piperazin-1-yl, 4-methyl-piperazin-1-yl, piperidin-1-yl, piperidin-4-yl, 4-benzyl-piperidin-1-yl, 2-methyl-piperidin-1-yl, 1-ethyl-pyrrolidin-2-yl, 1-methyl-pyrrolidin-2-yl, 2-oxo-pyrrolidin-1-yl, pyridin-2-yl, pyridin-4-yl, 5-nitro-pyridin-2-yl, imidazol-1-yl, morpholin-4-yl, 5-methoxy-1H-indol-2-yl, 5-(3-chlorophenyl)-furan-2-yl, 5-(4-fluorophenyl)-thiophen-2-yl, 5-(2-methoxyphenyl)-thiophen-2-yl, 5-(2-cyanophenyl)-thiophen-2-yl, 5-(2,5-dimethoxyphenyl)-thiophen-2-yl, 2-[2,2']bithiophenyl-5-yl, 2-(5-pyridin-4-yl-thiophen-2-yl, 5-(1H-indol-5-yl)-thiophen-2-yl, 5-quinolin-8-yl-thiophen-2-yl or 5-(benzo[b]thiophen-2-yl)-thiophen-2-yl,
Het$^2$ is thiophen-2-yl, pyridin-3-yl, pyridin-2-yl, pyridin-4-yl, indol-5-yl, quinolin-8-yl, 4,6-dimethoxy-pyrimidin-2-yl or benzo[b]thiophen-2-yl,
Hal is F, Cl, Br or I,
Ph is phenyl,
n is 1 or 2,
m is 0, 1 or 2,
o is 1, 2, 3 or 7,
p is 0 or 1 and
q is 1, 2 or 3;

in Ib-4
R and R$^1$ are independently of each other H, Hal, allyl, CH═CH—COOR$^5$, CH═CHCON(R$^5$)$_2$ or 4-methylphenyl,
R$^2$ and R$^3$ are independently of each other H, cyclohexylmethyl, —(CH$_2$)$_o$-Het$^1$, —(CHA)$_p$-(CH$_2$)$_o$—N(R$^5$)$_2$, —(CH$_2$)$_p$—(CHA)$_p$-(CH$_2$)$_m$—Ar or —(CH$_2$)$_o$—Z—(CH$_2$)$_q$—N(R$^5$)$_2$,
provided that R$^2$ and R$^3$ together are not H,
R$^4$ is Ar,
R$^5$ is H or A,
Y is (CH═CH)$_n$,
Z is phenylene, cyclohexylene, —NR$^5$, O, —CH(OH)—, —CA$_2$- or

A is unbranched or branched alkyl having 1 to 6 carbon atoms,
Ar is phenyl, which is mono-, di- or trisubstituted by O—(CH$_2$)$_p$-Ph, naphthyl or Het$^2$, or biphenyl, which is unsubstituted or mono-, di- or trisubstituted by A, OR$^5$, CF$_3$, Hal, COA, N(R$^5$)$_2$, NO$_2$, NR$^5$—COA or Het$^2$,
Het$^1$ is 4-methyl-piperazin-1-yl, imidazol-1-yl or morpholin-4-yl,
Het$^2$ is thiophen-2-yl, pyridin-3-yl or benzo[b]thiophen-2-yl,
Hal is F, Cl, Br or I,
Ph is phenyl,
n is 1 or 2,
m is 0, 1 or 2,
o is 1, 2, 3 or 7,
p is 0 or 1 and
q is 1, 2 or 3;

III. for group Ic in Ic-1
R and R$^1$ are independently of each other H, A, OR$^5$, Hal, N(R$^5$)$_2$, NO$_2$, CN, C(O)R$^2$, CON(R$^5$)$_2$, COOR$^5$, allyl, CH═CH—COOR$^5$, CH═CHCON(R$^5$)$_2$, SO$_2$A or phenyl, which is unsubstituted or mono-, di- or trisubstituted by A,
R$^2$ and R$^3$ are independently of each other H, A, cycloalkyl, -Het$^3$, —(CH$_2$)$_o$—OR$^5$, —(CH$_2$)$_o$—OR$^6$, —(CH$_2$)$_o$-Het$^1$, —(CH$_2$)$_o$—NR$^5$-Het$^1$, —(CHA)$_p$-(CH$_2$)$_o$—N(R$^5$)$_2$, —(CH$_2$)$_p$—(CHA)$_p$-(CH$_2$)$_m$—Ar, —(CH$_2$)$_o$—Z—(CH$_2$)$_q$—N(R$^5$)$_2$,

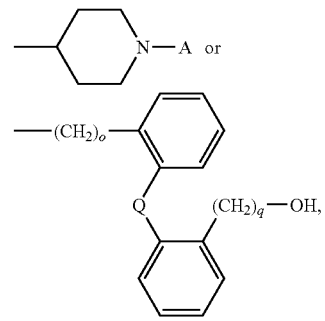

provided that R$^2$ and R$^3$ together are not H,
or NR$^2$R$^3$ together form a saturated monocyclic heterocyclic radical having 5 to 6 ring members, where 1 or 2 N atoms are present and the heterocyclic radical can be mono- or disubstituted by OH, Ar, OAr or arylalkyl,
R$^4$ is Het$^1$,
R$^5$ is H or A,
R$^6$ is benzo[1,3]dioxol-5-yl,
Q is O or S,
Y is (CH═CH)$_n$,
Z is phenylene, cyclohexylene, —NR$^5$—, O, —CH(OH)—, —CA$_2$- or

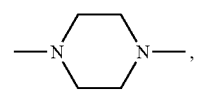

A is unbranched or branched alkyl having 1 to 6 carbon atoms,
Ar is phenyl, naphthyl or biphenyl, which is unsubstituted or mono-, di- or trisubstituted by A, OR$^5$, cycloalkyloxy, O—(CH$_2$)$_p$-Ph, CF$_3$, OCF$_3$, Hal, CN, CHO, COA, COOR$^5$, N(R$^5$)$_2$, NR$^5$—COA, NO$_2$, SO$_2$N(R$^5$)$_2$, mor, SO$_2$-mor, 5-methyl-3-oxo-2,4-dihydropyrazol-2-yl, naphthyl or Het$^2$,
Het$^1$ is a saturated, partially or completely unsaturated mono- or bicyclic heterocyclic radical having 5 to 10 ring members, where 1 or 2 N and/or 1 or 2 S or O atoms can be present and the heterocyclic radical can be mono- or disubstituted by A, Hal, OR$^5$, CF$_3$, OCF$_3$, N(R$^5$)$_2$, carbonyl oxygen, COOR$^5$, Het$^2$, benzyl or phenyl which is unsubstituted or mono-, di- or trisubstituted by A, OR$^5$, CF$_3$, OCF$_3$, Hal, CN, COOR$^5$, N(R$^5$)$_2$, NO$_2$ or SO$_2$N(R$^5$)$_2$, Het$^2$ is a unsaturated mono- or bicyclic heterocyclic radical having 5 to 10 ring members, where 1 or 2 N and/or 1 or 2 S or O atoms can be present and the heterocyclic radical can be mono- or disubstituted by A, Hal, OR$^5$, CF$_3$, OCF$_3$, N(R$^5$)$_2$ or COOR$^5$, Het$^3$ is a partially or completely unsaturated mono- or bicyclic heterocyclic radical having 5 to 10 ring members, where 1 or 2 N atoms are present and the heterocyclic radical can be mono- or disubstituted by A, Hal, OR$^5$, CF$_3$, OCF$_3$, N(R$^5$)$_2$, SO$_2$A or COOR$^5$ provided that the heterocyclic radical is not bonded via an N atom, Hal is F, Cl, Br or I,
mor is morpholin-4-yl,
Ph is phenyl,
n is 1 or 2,
m is 0, 1, 2, 3, 4, 5 or 6,
o is 1, 2, 3, 4, 5, 6 or 7,
p is 0, 1, 2, 3 or 4 and
q is 1, 2, 3 or 4;

in Ic-2
R and R$^1$ are independently of each other Hal, allyl, CH=CH—COOR$^5$, CH=CHCON(R$^5$)$_2$ or phenyl, which is unsubstituted or mono-, di- or trisubstituted by A,
R$^2$ and R$^3$ are independently of each other H, cycloalkyl, —(CH$_2$)$_o$-Het$^1$, —(CHA)$_p$-(CH$_2$)$_o$—N(R$^5$)$_2$ or —(CH$_2$)$_o$—Z—(CH$_2$)$_q$—N(R$^5$)$_2$, provided that R$^2$ and R$^3$ together are not H,
R$^4$ is Het$^1$,
R$^5$ is H or A,
Y is (CH=CH)$_n$,
Z is phenylene, cyclohexylene, —NR$^5$—, O, —CH(OH)—, —CA$_2$- or

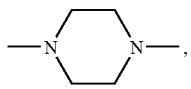

A is unbranched or branched alkyl having 1 to 6 carbon atoms,
Het$^1$ is a saturated, partially or completely unsaturated mono- or bicyclic heterocyclic radical having 5 to 10 ring members, where 1 or 2 N and/or 1 or 2 S or O atoms can be present and the heterocyclic radical can be mono- or disubstituted by A, Hal, OR$^5$, CF$_3$, OCF$_3$, N(R$^5$)$_2$, carbonyl oxygen, COOR$^5$, Het$^2$, benzyl or phenyl which is unsubstituted or mono-, di- or trisubstituted by A, OR$^5$, CF$_3$, OCF$_3$, Hal, CN, COOR$^5$, N(R$^5$)$_2$, NO$_2$ or SO$_2$N(R$^5$)$_2$,
Het$^2$ is a unsaturated mono- or bicyclic heterocyclic radical having 5 to 10 ring members, where 1 or 2 N and/or 1 or 2 S or O atoms can be present and the heterocyclic radical can be mono- or disubstituted by A, Hal, OR$^5$, CF$_3$, OCF$_3$, N(R$^5$)$_2$ or COOR$^5$,
Hal is F, Cl, Br or I,
n is 1 or 2,
o is 1, 2, 3 or 7,
p is 0, 1, 2 or 3 and
q is 1, 2 or 3;

in Ic-3
R and R$^1$ are independently of each other H or Hal,
R$^2$ and R$^3$ are independently of each other H, cycloalkyl, —(CH$_2$)$_o$-Het$^1$, —(CHA)$_p$-(CH$_2$)$_o$—N(R$^5$)$_2$ or —(CH$_2$)$_o$—Z—(CH$_2$)$_q$—N(R$^5$)$_2$, provided that R$^2$ and R$^3$ together are not H,
R$^4$ is Het$^1$,
R$^5$ is H or A,
Y is (CH=CH)$_n$,
Z is phenylene, cyclohexylene, —NR$^5$—, O, —CH(OH)—, —CA$_2$- or

A is unbranched or branched alkyl having 1 to 6 carbon atoms,
Het$^1$ is thiophen-2-yl, tetrahydro-furan-2-yl, 1-methyl-octahydro-indol-3-yl, benzo[1,3]dioxol-5-yl, piperazin-1-yl, 4-methyl-piperazin-1-yl, piperidin-1-yl, piperidin-4-yl, 4-benzyl-piperidin-1-yl, 2-methyl-piperidin-1-yl, 1-ethyl-pyrrolidin-2-yl, 1-methyl-pyrrolidin-2-yl, 2-oxo-pyrrolidin-1-yl, pyridin-2-yl, pyridin-4-yl, 5-nitro-pyridin-2-yl, imidazol-1-yl, morpholin-4-yl, 5-methoxy-1H-indol-2-yl, 5-(3-chlorophenyl)-furan-2-yl, 5-(4-fluorophenyl)-thiophen-2-yl, 5-(2-methoxyphenyl)-thiophen-2-yl, 5-(2-cyanophenyl)-thiophen-2-yl, 5-(2,5-dimethoxyphenyl)-thiophen-2-yl, 2-[2,2']bithiophenyl-5-yl, 2-(5-pyridin-4-yl-thiophen-2-yl, 5-(1H-indol-5-yl)-thiophen-2-yl, 5-quinolin-8-yl-thiophen-2-yl or 5-(benzo[b]thiophen-2-yl)-thiophen-2-yl,
Hal is F, Cl, Br or I,
n is 1 or 2,
o is 1, 2, 3 or 7,
p is 0, 1, 2 or 3 and
q is 1, 2 or 3;

in Ic-4
R and R$^1$ are independently of each other H or Hal,
R$^2$ and R$^3$ are independently of each other H, cycloalkyl, —(CH$_2$)$_o$-Het$^1$, —(CHA)$_p$-(CH$_2$)$_o$—N(R$^5$)$_2$ or —(CH$_2$)$_o$—Z—(CH$_2$)$_q$—N(R$^5$)$_2$, provided that R$^2$ and R$^3$ together are not H,
R$^4$ is 2-[2,2']bithiophenyl-5-yl or 5-(3-chlorophenyl)-furan-2-yl,
R$^5$ is H or A,
Y is (CH=CH)$_n$,
Z is phenylene, cyclohexylene, —NR$^5$—, O, —CH(OH)—, —CA$_2$- or

A is unbranched or branched alkyl having 1 to 6 carbon atoms,
Het$^1$ is thiophen-2-yl, tetrahydro-furan-2-yl, 1-methyl-octahydro-indol-3-yl, benzo[1,3]dioxol-5-yl, piperazin-1-yl, 4-methyl-piperazin-1-yl, piperidin-1-yl, piperidin-4-yl, 4-benzyl-piperidin-1-yl, 2-methyl-piperidin-1-yl, 1-ethyl-pyrrolidin-2-yl, 1-methyl-pyrrolidin-2-yl, 2-oxo-pyrrolidin-1-yl, pyridin-2-yl, pyridin-4-yl, 5-nitro-pyridin-2-yl, imidazol-1-yl, morpholin-4-yl, 5-methoxy-1H-indol-2-yl, 5-(3-chlorophenyl)-furan-2-yl, 5-(4-fluorophenyl)-thiophen-2-yl, 5-(2-methoxyphenyl)-thiophen-2-yl, 5-(2- cyanophenyl)-thiophen-2-yl, 5-(2,5-dimethoxyphenyl)-thiophen-2-yl, 2-[2,2']bithiophenyl-5-yl, 2-(5-pyridin-4-yl-thiophen-2-yl, 5-(1H-indol-5-yl)-thiophen-2-yl, 5-quinolin-8-yl-thiophen-2-yl or 5-(benzo[b]thiophen-2-yl)-thiophen-2-yl, Hal is F, Cl, Br or I,
n is 1 or 2,
o is 1, 2, 3 or 7,
p is 0, 1, 2 or 3 and
q is 1, 2 or 3;

in Ic-5
R and $R^1$ are independently of each other H or Hal,
$R^2$ and $R^3$ are independently of each other H, cycloalkyl, —(CH$_2$)$_o$-Het$^1$, —(CHA)$_p$-(CH$_2$)$_o$—N(R$^5$)$_2$ or —(CH$_2$)$_o$—Z—(CH$_2$)$_q$—N(R$^5$)$_2$, provided that $R^2$ and $R^3$ together are not H,
$R^4$ is 2-[2,2']bithiophenyl-5-yl,
$R^5$ is H or A,
Y is (CH=CH)$_n$,
Z is phenylene, cyclohexylene, —NR$^5$, O, —CH(OH)—, —CA$_2$- or

A is unbranched or branched alkyl having 1 to 6 carbon atoms,
Het$^1$ is piperidin-4-yl or pyridinyl,
Hal is F, Cl, Br or I,
n is 1,
o is 1, 2, 3 or 7,
p is 0, 1, 2 or 3 and
q is 1, 2 or 3.

The invention relates additionally to novel substituted 4-amino-quinazolines of the formula I according to group Ia and their pharmaceutically tolerable salts and solvates.

The invention relates additionally to novel substituted 4-amino-quinazolines of the formula I according to group Ib and their pharmaceutically tolerable salts and solvates.

The invention relates additionally to novel substituted 4-amino-quinazolines of the formula I according to group Ic and their pharmaceutically tolerable salts and solvates.

The invention relates further to novel substituted 4-amino-quinazolines of the formula I according to groups Ia-Ic and their pharmaceutically tolerable salts and solvates as a medicament.

The invention relates to novel substituted 4-amino-quinazolines of the formula I according to groups Ia-Ic and their pharmaceutically tolerable salts and solvates as a glycoprotein IbIX antagonist.

The invention relates further to novel special compounds of formula I selected from the group
a) (7-chloro-2-styryl-quinazolin-4-yl)-(3-imidazol-1-yl-propyl)-amine,
b) N'-(7-chloro-2-styryl-quinazolin-4-yl)-N,N-diethyl-ethane-1,2-diamine,
c) N'-(7-chloro-2-styryl-quinazolin-4-yl)-N,N-diethyl-propane-1,3-diamine,
d) (7-chloro-2-styryl-quinazolin-4-yl)-(3-morpholin-4-yl-propyl)-amine,
e) 1-[3-(7-chloro-2-styryl-quinazolin-4-ylamino)-propyl]-pyrrolidin-2-one,
f) [2-(4-amino-phenyl)-ethyl]-(7-chloro-2-styryl-quinazolin-4-yl)-amine,
g) N$^4$-{2-[2-(4-bromo-phenyl)-vinyl]-7-chloro-quinazolin-4-yl}-N',N'-diethyl-pentane-1,4-diamine and
h) N$^4$-[7-chloro-2-(4-phenyl-buta-1,3-dienyl)-quinazolin-4-yl]-N$^1$,N$^1$-diethyl-pentane-1,4-diamine and their pharmaceutically tolerable salts and solvates.

The invention relates further to the novel substituted 4-amino-quinazolines a) to h) of the formula I and their pharmaceutically tolerable salts and solvates as a medicament.

The invention relates to the novel substituted 4-amino-quinazolines a) to h) of the formula I and their pharmaceutically tolerable salts and solvates as a glycoprotein IbIX antagonist.

The compounds of the formula I and also the starting substances for their preparation are otherwise prepared by methods known per se, such as are described in the literature (e.g. in the standard works such as Houben-Weyl, Methoden der organischen Chemie [Methods of Organic Chemistry], Georg-Thieme-Verlag, Stuttgart), namely under reaction conditions which are known and suitable for the reactions mentioned. In this case, use can also be made of variants which are known per se, but not mentioned here in greater detail.

The starting substances, if desired, can also be formed in situ such that they are not isolated from the reaction mixture, but immediately reacted further to give the compounds of the formula I.

The compounds of the formula I according to claims 1 to 4 can be obtained by liberating them from their functional derivatives by solvolysis, in particular hydrolysis or by hydrogenolysis.

Preferred starting substances for the solvolysis or hydrogenolysis are those which otherwise correspond to the formula I according to claims 1 to 4, but instead of one or more free amino, and/or hydroxyl groups contain corresponding protected amino and/or hydroxyl groups, in particular those which instead of an H—N— group carry an R'—N— group, in which R' is an amino protective group and/or those which instead of the H atom of a hydroxyl group carry a hydroxyl protective group, e.g. those which correspond to the formula I, but instead of a group —COOH carry a group —COOR", in which R" is a hydroxyl protective group.

A number of—identical or different—protected amino and/or hydroxyl groups can also be present in the molecule of the starting substance. If the protective groups present are different from one another, in many cases they can be removed selectively (lit.: T. W. Greene, P. G. M. Wuts, *Protective Groups in Organic Chemistry*, 2nd ed., Wiley, New York 1991 or P. J. Kocienski, *Protecting Groups*, 1st ed., Georg Thieme Verlag, Stuttgart—New-York, 1994).

The expression "amino protective group" is generally known and relates to groups which are suitable for protecting (for blocking) an amino group against chemical reactions, but which are easily removable after the desired chemical reaction has been carried out at other positions in the molecule. Typical groups of this type are, in particular, unsubstituted or substituted acyl, aryl, aralkoxymethyl or aralkyl groups. Since the amino protective groups are removed after the desired reaction (or reaction sequence), their nature and size is otherwise not critical; however, those having 1-20, in particular 1-8, C atoms are preferred. The expression "acyl group" is to be interpreted in the widest sense in connection with the present process. It includes acyl groups derived from aliphatic, araliphatic, aromatic or heterocyclic carboxylic acids or sulfonic acids and, in particular, alkoxycarbonyl groups, aryloxycarbonyl groups and especially aralkoxycarbonyl groups. Examples of acyl groups of this type are alkanoyl such as acetyl, propionyl, butyryl; aralkanoyl such as phenylacetyl; aroyl such as benzoyl or toluoyl; aryloxyalkanoyl such as POA; alkoxycarbonyl such as methoxycarbonyl, ethoxycarbonyl, 2,2,2-trichloroethoxycarbonyl, BOC, 2-iodoethoxycarbonyl; aralkyloxycarbonyl such as CBZ ("carbobenzoxy"), 4-methoxybenzyloxycarbonyl (MOZ), 4-Nitro-benzyloxycarbonyl oder 9-fluorenylmethoxycarbonyl (Fmoc); 2-(phenylsulfonyl)ethoxycarbonyl; trimethylsilylethoxycarbonyl (Teoc) or arylsulfonyl such as 4-methoxy-2,3,6-trimethylphenyl-sulfonyl (Mtr). Preferred amino protective groups are BOC, furthermore CBZ, Fmoc, benzyl and acetyl; particularly preferred Fmoc.

The expression "hydroxyl protective group" is also generally known and relates to groups which are suitable for protecting a hydroxyl group against chemical reactions, but which are easily removable after the desired chemical reaction has been carried out at other positions in the molecule.

Typical groups of this type are the above mentioned unsubstituted or substituted aryl, aralkyl, aroyl or acyl groups, furthermore also alkyl groups, alkyl-, aryl- or aralkylsilyl groups or O,O- or O,S-acetals. The nature and size of the hydroxyl protective groups is not critical, since they are removed again after the desired chemical reaction or reaction sequence; groups having 1-20, in particular 1-10 C atoms, are preferred. Examples of hydroxyl protective groups are, inter alia, benzyl, 4-methoxybenzyl or 2,4-dimethoxybenzyl, aroyl groups such as benzoyl or p-nitrobenzoyl, acyl groups such as acetyl or pivaloyl, p-toluylsulfonyl, alkyl groups such as methyl or tert-butyl, but also allyl, alkylsilyl groups such as trimethylsilyl (TMS), triisopropylsilyl (TIPS), tert-butyldimethylsilyl (TBS) or triethylsilyl, trimethylsilylethyl, aralkylsilyl groups such as tert-butyldiphenylsilyl (TBDPS), cyclic acetals such as isopropylidene-, cyclopentylidene-, cyclohexylidene-, benzylidene-, p-methoxybenzylidene- or o,p-dimethoxybenzylideneacetal, acyclic acetales such as tetrahydropyranyl (Thp), methoxymethyl (MOM), methoxyethoxymethyl (MEM), benzyloxymethyl (BOM) or methylthiomethyl (MTM). Acetyl, benzyl, tert-butyl or TBS being particularly preferred.

The liberation of the compounds of the formula I from their functional derivatives depending on the protective group used is known in the present literature such as T. W. Greene, P. G. M. Wuts, *Protective Groups in Organic Chemistry*, 2nd ed., Wiley, New York 1991, P. J. Kocienski, *Protecting Groups*, 1st ed., Georg Thieme Verlag, Stuttgart—New-York, 1994. In this case, use can also be made of variants which are known per se, but not mentioned here in greater detail.

The groups BOC and O-tert-butyl can preferably be removed, for example, using TFA in dichloromethane or using approximately 3 to 5N HCl in dioxane at 15-30° C., the Fmoc group using an approximately 5 to 50% solution of dimethylamine, diethylamine or piperidine in DMF at 15-30° C.

Preferred starting substances for the solvolysis or hydrogenolysis includes also those which otherwise correspond to the formula I, but are attached to a solid phase. The liberation of the compounds of the formula I from the solid phase is known in the present literature such as Novabiochem—The Combinatorial Chemistry Catalog, March 99 and cited literature.

The solid phase with a carbonate moiety as terminal functional group can preferably be removed, for example, using TFA (50%) in dichloromethane.

The quinazolines of formula I according to claims 1 to 4 can also preferably be prepared, using either solution or solid-phase techniques.

The term solid phase indicates a resin for solid-phase chemistry, especially for combinatorial chemistry, i.e. by robot- and computer-assisted syntheses, and subjected to mass screening as indicated in U.S. Pat. No. 5,463,564; M. A. Gallop et al., J. Med. Chem. 1994; 37, 1233-1251 and 1385-1401 and M. J. Sofia, Drug Discovery Today 1996, 1, 27-34). The polymeric material of the solid phase is generally chosen from the group consisting of cross-linked polystyrene, cross-linked polyacrylamide or other resins, natural polymers or silicagels.

The group of cross-linked polystyrene, cross-linked polyacrylamide or other resins includes e.g. polyacrylamide, polymethacrylamide, polyhydroxyethylmethacrylate, polyamide, polystyrene, (meth)acrylate copolymers, for instance from (methy)acrylic acid, esters of (meth)acrylic acid and/or 2-methylene-succinic acid, but-2-enoic acid or maleic acid, polyurethanes or other copolymers.

Suitable terminal functional groups or linkers on the surface of the resin have to be chosen to attach the compounds to the resin. There exists a variety of commercially available resins, e.g. in Novabiochem—The Combinatorial Chemistry Catalog, March 99. Examples for suitable resins are carbonate resins with a modified carbonate group as terminal functional group like p-nitrophenylcarbonate resin, halogenated resins like Merrifield resin (chloromethylpolystyrene) or carboxy resins like carboxy polystyrene resin or NovaSyn® TG Carboxy Resin. p-Nitrophenylcarbonate resin is particularly preferred. These and other types of resins well known in the art can be used in the subject invention.

The quinazolines of formula I according to claims 1 to 4 can therefore preferably be prepared by combining and reacting a 2-methyl-3H-quinazolin-4-one of formula II with an aldehyde of formula III, chlorinating the given formula IV and reacting the given formula V with an amine of formula VI.

The quinazolines of formula I according to claims 1 to 4 can furthermore be prepared by chlorinating a 2-methyl-3H-quinazolin-4-one of formula II, reacting the given formula VII with the amine of formula VI and reacting the given formula VIII with an aldehyde of formula III.

As a rule, the starting compounds of the formulae II, III and VI are known or commercially available.

The unknown compounds, however, can be prepared by methods known per se.

The 2-methyl-3H-quinazolin-4-ones of formula II in which R and $R^1$ have a meaning indicated in claims 1 to 4 can be prepared by reacting a substituted anthranilic acid with acetic anhydride and reacting the given 2-methyl-benzoxazin-4-one with ammonium acetate.

The aldehydes of formula II, as a rule, are also commercially available. Furthermore, syntheses for the preparation of aldehydes of formula III, such as, for example, the oxidation of an alcohol, can be used.

The amines of formula VI in which $R^2$ or $R^3$ have a meaning indicated in claims 1 to 4, as a rule, are also commercially available and can be attached to the suitable resin or to a compound of formula V or VII by coupling procedures well known in the art and as described in the ensuing Examples. Furthermore, syntheses for the preparation of amines of formula III, such as, for example, the Gabriel synthesis, can be used.

For the preparation of compounds of the formula I in which $R^4$ is unsubstituted or, substituted biphenyl, aryl substituted furanyl or 5-[2,2']bithiophenyl, an appropriate compound of the formula I in which $R^4$ is phenyl chloride, phenyl bromide, phenyl iodide, furanyl chloride, furanyl bromide, furanyl iodide, thiophenyl chloride, thiophenyl bromide or thiophenyl iodide can be reacted with the appropriate boronic acid derivatives in a Suzuki type coupling reaction. This reaction is expediently carried out under Palladium catalysis with different phosphines as coordination ligands, e.g. $Pd(P(Ph)_3)_2$, $Pd(II)Cl_2dppf$, $PdOAc_2+P(R^*)_3$ ($R^*$=phenyl, cyclohexyl, tert-butyl) etc. in the presence of a base such as potassium carbonate, cesium carbonate, DBU, NaOH, in an inert solvent or solvent mixture, e.g. DMF or 1,4-dioxane at temperatures between 0° and 150°, preferably between 60° and 120°. Depending on the conditions used, the reaction time is between a few minutes and a number of days. The boronic acid derivatives can be prepared by conventional methods or are commercially available. The reactions can be carried out in analogy to the methods indicated in Suzuki et al., J. Am. Chem. Soc. 1989, 111, 314 ff., Suzuki et al., Chem. Rev. 1995, 95, 2457 ff and G. C. Fu et al. Angew. Chem. 1998, 110, 3586.

The Suzuki type coupling reaction can be furthermore used to convert radicals R and $R^1$ into other radicals R and $R^1$, for e.g. to convert a halogen substituted quinazolines to a quinazoline substituted by substituted or unsubstituted phenyl.

For the preparation of compounds of the formula I in which R or $R^1$ is allyl, an appropriate compound of the formula I in which $R^4$ is quinazoline chloride, quinazoline bromide or quinazoline iodide can be reacted with allyltributyltin in a Stille type coupling reaction. This reaction is expediently carried out under Palladium catalysis with different phosphines as coordination ligands, e.g. $Pd(P(Ph)_3)_2$, $Pd(II)Cl_2dppf$, $PdOAc_2+P(R^*)_3$ ($R^*$=phenyl, cyclohexyl, tert-butyl) etc. in an inert solvent or solvent mixture, e.g. DMF or 1,4-dioxane at temperatures between 0° and 150°, preferably between 60° and 120°. Depending on the conditions used, the reaction time is between a few minutes and a number of days.

For the preparation of compounds of the formula I in which R or $R^1$ is CH=CH—$COOR^5$ or CH=CH—$CON(R^5)_2$, an appropriate compound of the formula I in which $R^4$ is quinazoline chloride, quinazoline bromide or quinazoline iodide can be reacted with substituted acrylate in a Heck type coupling reaction. This reaction is expediently carried out under Palladium catalysis with different phosphines as coordination ligands, e.g. $Pd(P(Ph)_3)_2$, $Pd(II)Cl_2dppf$, $PdOAc_2+P(R^*)_3$ ($R^*$=phenyl, cyclohexyl, tert-butyl) etc. in the presence of a base such as triethyl amine or a catalyst tetrabutylammonium iodide, in an inert solvent or solvent mixture, e.g. DMF or 1,4-dioxane at temperatures between 0° and 150°, preferably between 60° and 120°. Depending on the conditions used, the reaction time is between a few minutes and a number of days.

A base of the formula I can be converted into the associated acid addition salt using an acid, for example by reaction of equivalent amounts of the base and of the acid in an inert solvent such as ethanol and subsequent evaporation. Acids which give physiologically acceptable salts are particularly suitable for this reaction. Thus inorganic acids can be used, e.g. sulfuric acid, nitric acid, hydrohalic acids such as hydrochloric acid or hydrobromic acid, phosphoric acids such as orthophosphoric acid, sulfamic acid, furthermore organic acids, in particular aliphatic, alicyclic, araliphatic, aromatic or heterocyclic mono- or polybasic carboxylic, sulfonic or sulfuric acids, e.g. formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, p-toluenesulfonic acid, naphthalene mono- and disulfonic acids or laurylsulfuric acid. Salts with physiologically unacceptable acids, e.g. picrates, can be used for the isolation and/or purification of the compounds of the formula I.

On the other hand, compounds of the formula I with bases (e.g. sodium or potassium hydroxide or carbonate) can be converted into the corresponding metal salts, in particular alkali metal or alkaline earth metal salts, or into the corresponding ammonium salts.

The invention furthermore relates to pharmaceutical preparations comprising at least one compound of the formula I according to Claims 1 to 5 and/or one of its physiologically acceptable salts, which are prepared, in particular, in an non-chemical way. In this case, the compounds of the formula I according to the invention can be brought into a suitable dose form together with at least one solid, liquid and/or semi-liquid excipient or auxiliary and, if appropriate, in combination with one or more other active compounds.

These preparations can be used as medicaments in human or veterinary medicine. Possible excipients are organic or inorganic substances which are suitable for enteral (e.g. oral) or parenteral administration or topical application and do not react with the novel compounds, for example water, vegetable oils, benzyl alcohols, alkylene glycols, polyethylene glycols, glyceryl triacetate, gelatin, carbohydrates such as lactose or starch, magnesium stearate, talc and petroleum jelly. Tablets, pills, coated tablets, capsules, powders, granules, syrups, juices or drops are used, in particular, for oral administration, suppositories are used for rectal administration, solutions, preferably oily or aqueous solutions, furthermore suspensions, emulsions or implants, are used for parenteral administration, and ointments, creams or powders are used for topical application. The novel compounds can also be lyophilized and the lyophilizates obtained used, for example, for the production of injection preparations. The preparations indicated can be sterilized and/or can contain auxiliaries such as lubricants, preservatives, stabilizers and/or wetting agents, emulsifiers, salts for affecting the osmotic pressure, buffer substances, colorants, flavorings and/or one or more other active compounds, e.g. one or more vitamins.

The compounds of the formula I and their physiologically acceptable salts according to claims 1 to 5 act as adhesion receptor antagonists, in particular glycoprotein IbIX antagonists, and can be employed for the prophylaxis and/or therapy of thrombotic disorders and sequelae deriving therefrom. The disorders are acute coronary syndromes, angina pectoris, myocardial infarct, peripheral circulatory disorders, stroke, transient ischaemic attacks, arteriosclerosis and reocclusion/restenosis after angioplasty/stent implantation.

In this case, the substances according to the invention are as a rule administered in the dose of the glycoprotein IIbIIIa antagonist ReoPro® of preferably between approximately 1 and 500 mg, in particular between 5 and 100 mg, per dose unit. The daily dose is preferably between approximately 0.02 and 10 mg/kg of body weight. The specific dose for each patient depends, however, on all sorts of factors, for example on the efficacy of the specific compound employed, on the age, body weight, general state of health and sex, on the diet, on the time and route of administration, and on the excretion rate, pharmaceutical combination and severity of the particular disorder to which the therapy applies. Oral administration is preferred.

Above and below, all temperatures are indicated in ° C. In the following examples, "customary working-up" for solution reactions means: if necessary, water is added, if necessary, depending on the constitution of the final product, the mixture is adjusted to pHs between 2 and 10 and extracted with ethyl acetate or dichloromethane, the organic phase is separated off, dried over sodium sulfate and evaporated, and the residue is purified by chromatography on silica gel and/or by crystallization.

"Customary working-up" for solid-phase reactions means: the crude reaction is filtered and washed with DMF twice, then successively with methanol and methylene chloride three times, and finally once with methyl tert-butyl ether. The resin is then dried in vacuo.

Mass spectrometry (MS) apparatuses OMIT and Finnigan LCQ. (M+H)+ values or M+ values are determined.

EXAMPLES

Example 1

(3-Aminomethyl-cyclohexylmethyl)-[2-(2-naphthalen-1-yl-vinyl)-quinazolin-4-yl]-amine 1. Anthranilic acid (0.29 mole) is added to 170 ml acetic anhydride. The solution is heated to 140° for 3 h. After cooling to room temperature (rt), the white solid is collected by filtration and washed with diethyl ether. Air drying give 2-methylbenzoxazin-4-one.

2. 2-Methylbenzoxazin-4-one (0.24 mole) and ammonium acetate (0.30 mole) is given in 50 ml of N,N-dimethylacetamide and then heated to 160° under a nitrogen blanket for 2 h. After cooling to rt, the white solid is collected by filtration and washed with diethyl ether. Air drying give 2-methyl-quinazolin-4-one.

3. 2-Methylquinazolin-4-one (50 mmol) and naphthalene-1-carbaldehyde (54 mmol) are suspended in 80 ml acetic acid. The mixture is heated to 100° for 24 h. After cooling to rt, the product crystallize out. After filtration, washing with ethyl acetate and air drying, 2-(2-naphthalen-1-yl-vinyl)-3H-quinazolin-4-one is given.

4. 2-(2-Naphthalen-1-yl-vinyl)-3H-quinazolin-4-one (11 mmol), phosphorus oxychloride (20 ml) and N,N-diethylaniline (1.0 ml) is added to a round-bottomed flask. The mixture is heated at 110° for 12 h. After cooling to rt, the reaction is quenched with ice-water and the crude product is collected by suction filtration. The crude solid is dissolved in ethyl acetate. Customary working up afforded 4-chloro-2-(2-naphthalen-1-yl-vinyl)-3,4-dihydro-quinazoline.

5. 4-Chloro-2-(2-naphthalen-1-yl-vinyl)-3,4-dihydro-quinazoline (0.08 mmol), C-(3-aminomethyl-cyclohexyl)-methylamine (0.24 mmol) and 2 ml ethyl alcohol are placed in an 8 ml glass vial sealed with a teflon-lined screw cap. The mixture is heated at 80° for 3 hrs. After cooling to rt, the ethyl alcohol is removed. Ethyl acetate (3 ml) and water (3 ml) are added to the vial. After agitation, the water was removed. The procedure is repeated with water and aq. NaCl (sat.). Purification with silica gel afforded (3-aminomethyl-cyclohexylmethyl)-[2-(2-naphthalen-1-yl-vinyl)-quinazolin-4-yl]-amine;
MS calc.: 422.6; found: 423.5.

Example 2

Analogously to example 1, 2-methylquinazolin-4-one is reacted with 4-pentyloxy-benzaldehyde, chlorinated and reacted with C-(3-aminomethyl-cyclohexyl)-methylamine to obtain (3-aminomethyl-cyclohexylmethyl)-{2-[2-(4-pentyloxy-phenyl)-vinyl]-quinazolin-4-yl}-amine;
MS calc.: 458.6; found: 459.5;

with 3-phenyl-propenal, chlorinated and reacted with C-(3-aminomethyl-cyclohexyl)-methylamine to obtain (3-aminomethyl-cyclohexylmethyl)-[2-(4-phenyl-buta-1,3-dienyl)-quinazolin-4-yl]-amine;
MS calc.: 398.6; found: 399.4;

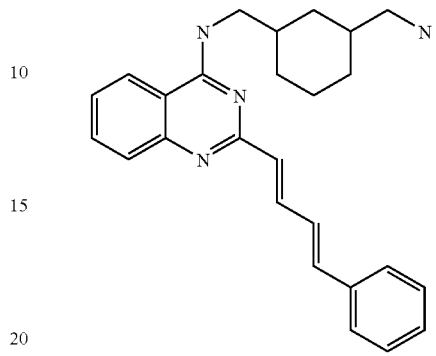

with 3-fluoro-benzaldehyde, chlorinated and reacted with C-(3-aminomethyl-cyclohexyl)-methylamine to obtain (3-aminomethyl-cyclohexylmethyl)-{2-[2-(3-fluoro-phenyl)-vinyl]-quinazolin-4-yl}-amine;
MS calc.: 390.5; found: 391.4;

with 2-fluoro-benzaldehyde, chlorinated and reacted with C-(3-aminomethyl-cyclohexyl)-methylamine to obtain (3-aminomethyl-cyclohexylmethyl)-{2-[2-(2-fluoro-phenyl)-vinyl]-quinazolin-4-yl}-amine;
MS calc.: 390.5; found: 391.3;

with 4-chloro-benzaldehyde, chlorinated and reacted with C-(3-aminomethyl-cyclohexyl)-methylamine to obtain (3-aminomethyl-cyclohexylmethyl)-{2-[2-(4-chloro-phenyl)-vinyl]-quinazolin-4-yl}-amine;
MS calc.: 407.0; found: 410.3;

with 3-chloro-benzaldehyde, chlorinated and reacted with C-(3-aminomethyl-cyclohexyl)-methylamine to obtain (3-aminomethyl-cyclohexylmethyl)-{2-[2-(3-chloro-phenyl)-vinyl]-quinazolin-4-yl}-amine;
MS calc.: 407.0; found: 407.3;

with 4-amino-benzaldehyde, chlorinated and reacted with C-(3-aminomethyl-cyclohexyl)-methylamine to obtain (3-aminomethyl-cyclohexylmethyl)-{2-[2-(4-amino-phenyl)-vinyl]-quinazolin-4-yl}-amine;
MS calc.: 387.5; found: 388.4;

with 4-methoxy-benzaldehyde, chlorinated and reacted with C-(3-aminomethyl-cyclohexyl)-methylamine to obtain (3-aminomethyl-cyclohexylmethyl)-{2-[2-(4-methoxy-phenyl)-vinyl]-quinazolin-4-yl}-amine;
MS calc.: 402.5; found: 403.3;

with 3-methoxy-benzaldehyde, chlorinated and reacted with C-(3-aminomethyl-cyclohexyl)-methylamine to obtain (3-aminomethyl-cyclohexylmethyl)-{2-[2-(3-methoxy-phenyl)-vinyl]-quinazolin-4-yl}-amine;
MS calc.: 402.5; found: 403.3;

with 4-methyl-benzaldehyde, chlorinated and reacted with C-(3-aminomethyl-cyclohexyl)-methylamine to obtain (3-aminomethyl-cyclohexylmethyl)-{2-[2-(4-methyl-phenyl)-vinyl]-quinazolin-4-yl}-amine;
MS calc.: 386.5; found: 387.3;

with 3-methyl-benzaldehyde, chlorinated and reacted with C-(3-aminomethyl-cyclohexyl)-methylamine to obtain (3-aminomethyl-cyclohexylmethyl)-{2-[2-(3-methyl-phenyl)-vinyl]-quinazolin-4-yl}-amine;
MS calc.: 386.5; found: 387.3;

with 2-methyl-benzaldehyde, chlorinated and reacted with C-(3-aminomethyl-cyclohexyl)-methylamine to obtain (3-aminomethyl-cyclohexylmethyl)-{2-[2-(2-methyl-phenyl)-vinyl]-quinazolin-4-yl}-amine;
MS calc.: 386.5; found: 387.3;

with 2-nitro-benzaldehyde, chlorinated and reacted with C-(3-aminomethyl-cyclohexyl)-methylamine to obtain (3-aminomethyl-cyclohexylmethyl)-{2-[2-(2-nitro-phenyl)-vinyl]-quinazolin-4-yl}-amine;
MS calc.: 417.5; found: 418.3;

with 3-nitro-benzaldehyde, chlorinated and reacted with C-(3-aminomethyl-cyclohexyl)-methylamine to obtain (3-aminomethyl-cyclohexylmethyl)-{2-[2-(3-nitro-phenyl)-vinyl]-quinazolin-4-yl}-amine;
MS calc.: 417.5; found: 418.3;

with 4-nitro-benzaldehyde, chlorinated and reacted with C-(3-aminomethyl-cyclohexyl)-methylamine to obtain (3-aminomethyl-cyclohexylmethyl)-{2-[2-(4-nitro-phenyl)-vinyl]-quinazolin-4-yl}-amine;
MS calc.: 417.5; found: 418.3;

with 3,4,5-trimethoxy-benzaldehyde, chlorinated and reacted with C-(3-aminomethyl-cyclohexyl)-methylamine to obtain (3-aminomethyl-cyclohexylmethyl)-{2-[2-(3,4,5-trimethoxy-phenyl)-vinyl]-quinazolin-4-yl}-amine;

with 4-carboxy-benzaldehyde, chlorinated and reacted with C-(3-aminomethyl-cyclohexyl)-methylamine to obtain (3-aminomethyl-cyclohexylmethyl)-{2-[2-(4-carboxy-phenyl)-vinyl]-quinazolin-4-yl}-amine;
MS calc.: 416.5; found: 417.3 and with 3-carboxy-benzaldehyde, chlorinated and reacted with C-(3-aminomethyl-cyclohexyl)-methylamine to obtain (3-aminomethyl-cyclohexylmethyl)-{2-[2-(3-carboxy-phenyl)-vinyl]-quinazolin-4-yl}-amine;
MS calc.: 416.5; found: 417.3.

Analogously to example 1, 7-chloro-2-methylquinazolin-4-one is reacted with 4-bromo-benzaldehyde, chlorinated and reacted with C-(3-aminomethyl-cyclohexyl)-methylamine to obtain (3-aminomethyl-cyclohexylmethyl)-{2-[2-(4-bromo-phenyl)-vinyl]-7-chloro-quinazolin-4-yl}-amine;
MS calc.: 485.9; found: 487.2.

Example 3

Analogously to example 1, 7-chloro-2-methylquinazolin-4-one is reacted with 3-phenoxy-benzaldehyde, chlorinated and reacted with $N^1,N^1$-diethyl-pentane-1,4-diamine to obtain $N^4$-{7-chloro-2-[2-(3-phenoxy-phenyl)-vinyl]-quinazolin-4-yl}$N^1,N^1$-diethyl-pentane-1,4-diamine;

with C-(3-aminomethyl-cyclohexyl)-methylamine to obtain (3-aminomethyl-cyclohexylmethyl)-{7-chloro-2-[2-(3-phenoxy-phenyl)-vinyl]-quinazolin-4-yl}-amine;
MS calc.: 499.1; found: 499.5;

with 3-aminomethyl-benzylamine to obtain (3-aminomethyl-benzyl)-{7-chloro-2-[2-(3-phenoxy-phenyl)-vinyl]-quinazolin-4-yl}-amine;
MS calc.: 493.0; found: 493.4 and with heptane-1,7-diamine
$N^1$-{7-chloro-2-[2-(3-phenoxy-phenyl)-vinyl]-quinazolin-4-yl}-heptane-1,7-diamine;
MS calc.: 487.0; found: 487.5.

Example 4

Analogously to example 1, 2-methylquinazolin-4-one is reacted with 4-benzyloxy-benzaldehyde, chlorinated and reacted with C-(3-aminomethyl-cyclohexyl)-methylamine to obtain (3-aminomethyl-cyclohexylmethyl)-{2-[2-(4-benzyloxy-phenyl)-vinyl]-quinazolin-4-yl}-amine;
MS calc.: 478.6 found: 479.4;

with 3-(3-amino-propoxy)-propylamine to obtain [3-(3-amino-propoxy)-propyl]-{2-[2-(4-benzyloxy-phenyl)-vinyl]-quinazolin-4-yl}-amine;
MS calc.: 468.6; found: 469.3;

with 2,2-dimethyl-propane-1,3-diamine to obtain $N^1$-{2-[2-(4-benzyloxy-phenyl)-vinyl]-quinazolin-4-yl}-2,2-dimethyl-propane-1,3-diamine;
MS calc.: 438.6; found: 439.3;

with $N^1$-(2-diethylamino-ethyl)-ethane-1,2-diamine to obtain
N-{2-[2-(4-benzyloxy-phenyl)-vinyl]-quinazolin-4-yl}-N'-(2-diethylamino-ethyl)-ethane-1,2-diamine;
MS calc.: 495.7; found: 496.3;

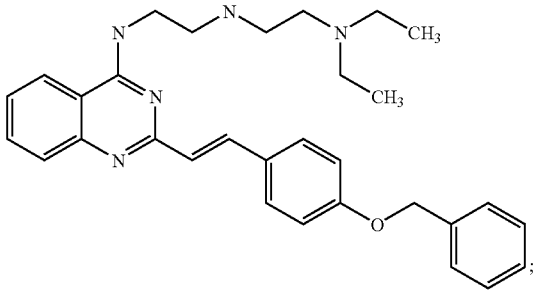

with heptane-1,7-diamine to obtain
$N^1$-{2-[2-(4-benzyloxy-phenyl)-vinyl]-quinazolin-4-yl}-heptane-1,7-diamine;
MS calc.: 466.6; found: 467.3;

with 4-(2-amino-ethyl)-phenylamine to obtain
[2-(4-amino-phenyl)-ethyl]-{2-[2-(4-benzyloxy-phenyl)-vinyl]-quinazolin-4-yl}-amine;
MS calc.: 472.6; found: 473.2;

with 3-morpholin-4-yl-propylamine to obtain
{2-[2-(4-benzyloxy-phenyl)-vinyl]-quinazolin-4-yl}-(3-morpholin-4-yl-propyl)-amine;
MS calc.: 480.6; found: 481.3;

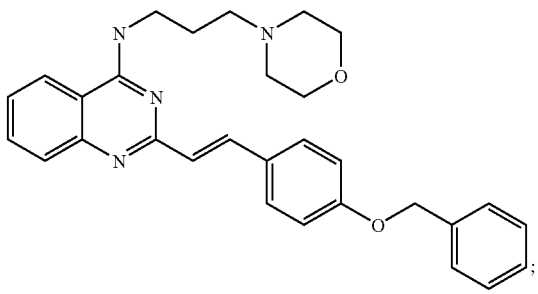

with N$^1$,N$^1$-diethyl-propane-1,3-diamine to obtain
N'-{2-[2-(4-benzyloxy-phenyl)-vinyl]-quinazolin-4-yl}-N,
N-diethyl-propane-1,3-diamine;
MS calc.: 466.6; found: 467.3;

with N$^1$,N$^1$-diethyl-ethane-1,2-diamine to obtain
N'-{2-[2-(4-benzyloxy-phenyl)-vinyl]-quinazolin-4-yl}-N,
N-diethyl-ethane-1,2-diamine;
MS calc.: 452.6; found: 453.2;

with 3-imidazol-1-yl-propylamine to obtain
{2-[2-(4-benzyloxy-phenyl)-vinyl]-quinazolin-4-yl}-(3-imidazol-1-yl-propyl)-amine;
MS calc.: 461.6; found: 462.2;

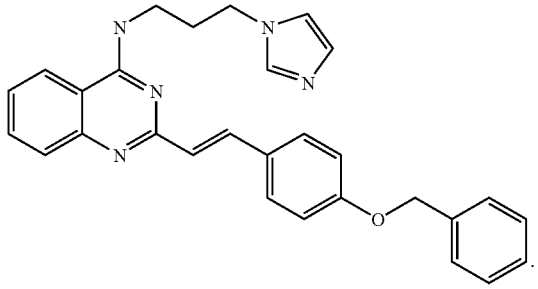

Analogously to example 1, 7-chloro-2-methylquinazolin-4-one is reacted with 4-benzyloxy-benzaldehyde, chlorinated and reacted with N$^1$,N$^1$-diethyl-pentane-1,4-diamine to obtain
N$^4$-{2-[2-(4-benzyloxy-phenyl)-vinyl]-7-chloro-quinazolin-4-yl}-N$^1$,N$^1$-diethyl-pentane-1,4-diamine;

with C-(3-aminomethyl-cyclohexyl)-methylamine to obtain
(3-aminomethyl-cyclohexylmethyl)-{2-[2-(4-benzyloxy-phenyl)-vinyl]-7-chloro-quinazolin-4-yl}-amine;
MS calc.: 513.1; found: 513.3.

Analogously to example 1, 6-iodo-2-methylquinazolin-4-one is reacted with 4-benzyloxy-benzaldehyde, chlorinated and reacted with N$^1$,N$^1$-diethyl-pentane-1,4-diamine to obtain
N$^4$-{2-[2-(4-benzyloxy-phenyl)-vinyl]-6-iodo-quinazolin-4-yl}-N$^1$,N$^1$-diethyl-pentane-1,4-diamine;
MS calc.: 620.6; found: 621.1;

with C-(3-aminomethyl-cyclohexyl)-methylamine to obtain
(3-aminomethyl-cyclohexylmethyl)-{2-[2-(4-benzyloxy-phenyl)-vinyl]-6-iodo-quinazolin-4-yl}-amine;
MS calc.: 604.5; found: 605.2.

Analogously to example 1, 6-bromo-2-methylquinazolin-4-one is reacted with 4-benzyloxy-benzaldehyde, chlorinated and reacted with N$^1$,N$^1$-diethyl-pentane-1,4-diamine to obtain
N$^4$-{2-[2-(4-benzyloxy-phenyl)-vinyl]-6-bromo-quinazolin-4-yl}-N$^1$,N$^1$-diethyl-pentane-1,4-diamine;
MS calc.: 573.6; found: 575.1;

with C-(3-aminomethyl-cyclohexyl)-methylamine to obtain
(3-aminomethyl-cyclohexylmethyl)-{2-[2-(4-benzyloxy-phenyl)-vinyl]-6-bromo-quinazolin-4-yl}-amine;
MS calc.: 557.5; found: 559.2.

Example 5

3-{4-[(3-Aminomethyl-cyclohexylmethyl)-amino]-2-[2-(4-benzyloxy-phenyl)-vinyl]-quinazolin-6-yl}-acrylic acid ethyl ester 1. Synthesis of Resin-Bound (3-aminomethyl-cyclohexylmethyl)-carbamate (1)

p-Nitrophenyl carbonate Wang resin (2.7 mmol, 0.54 mmol/g), 1,3-cyclohexane-bis(dimethylamine) (2.18 g, 15 mmol) and 75 ml DMF (dimethylformamide) are added to a sealed fritted polypropylene tube. The mixture is agitated for 72 h. After evacuation of the solvent, the resin is customary worked up for solid phase reactions.

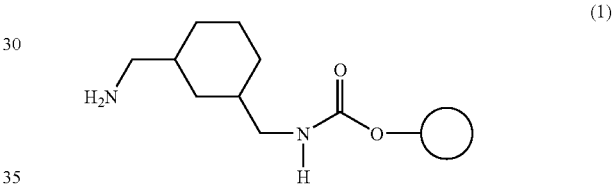

2. Analogously to example 1, 6-iodo-2-methylquinazolin-4-one is reacted with 4-benzyloxy-benzaldehyde and chlorinated to obtain 2-[2-(4-benzyloxy-phenyl)-vinyl]-4-chloro-6-iodo-quinazoline.

3. The resin-bound carbamate (1) (4.8 g, 0.54 mmol/g), 2-[2-(4-benzyloxy-phenyl)-vinyl]-4-chloro-6-iodo-quinazoline (6.6 mmol), triethylamine (1 ml) and 50 ml DMF are placed in a fritted polypropylene tube. The mixture is stirred at 80° for 60 hrs. After cooling to rt, the resin is customary worked up for solid phase reactions. Resin bound carbamate (2) is obtained.

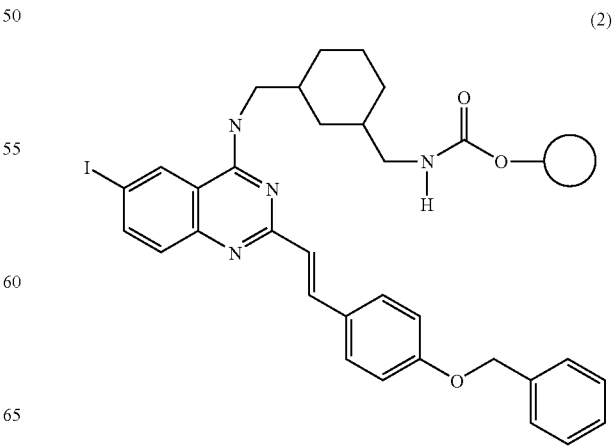

4. The solid supported 6-iodoquinazoline (2) (0.054 mmol, 0.54 mmol/g), ethyl acrylate (50 mg, 0.5 mmol), Pd(PPh$_3$)$_4$ (20 mg), Bu$_4$NI (tetra-butylammonium-iodide, 32 mg, 0.08 mmol) and 2 ml DMF are placed in a fritted polypropylene tube. The mixture is agitated at 80° for 24 h. After cooling to rt, the solvent is evacuated and the resin is customary worked up for solid phase reactions. The solid supported 6-ethoxy-acrylquinazoline and 2 ml of a mixture of H$_2$O, TFA (trifluoracetic acid) and dichloromethane (1:49:50) is placed in a fritted polypropylene tube. The contents are shaken for 2 h at rt. The suspension is filtered and the resin is washed with dichloromethane (1 ml) and methanol (1 ml) respectively. Evaporation of the combined filtrates give 3-{4-[(3-aminomethyl-cyclohexylmethyl)-amino]-2-[2-(4-benzyloxy-phenyl)-vinyl]-quinazolin-6-yl}-acrylic acid ethyl ester;

MS calc.: 576.7; found: 577.3.

Analogously to example 5.4, solid supported 6-iodoquinazoline (2) is reacted with N,N-dimethyl-acrylamide to obtain 3-{4-[(3-aminomethyl-cyclohexylmethyl)-amino]-2-[2-(4-benzyloxy-phenyl)-vinyl]-quinazolin-6-yl}-N,N-dimethyl-acrylamide;

MS calc.: 575.8; found: 576.4.

Example 6

Solid supported 6-iodoquinazoline (2) [synthesized according to example 5] (0.054 mmol, 0.54 mmol/g), allyl-tributyltin (140 mg, 0.5 mmol), Pd(PPh$_3$)$_4$ (20 mg), and 2 ml DMF are placed in a fritted polypropylene tube. The mixture is agitated at 80° got 24 h. After cooling to rt, the mixture is customary worked up for solid phase reactions. The solid supported 6-allylquinazoline and 2 ml of a mixture of H$_2$O, TFA and dichloromethane (1:49:50) is placed in a fritted polypropylene tube. The contents are shaken for 2 h at rt. The suspension is filtered and the resin is washed with dichloromethane (1 ml) and methanol (1 ml) respectively. Evaporation of the combined filtrates give {6-allyl-2-[2-(4-benzyloxy-phenyl)-vinyl]-quinazolin-4-yl}-(3-aminomethyl-cyclohexylmethyl)-amine;

MS calc.: 518.7; found: 519.3.

Example 7

Solid supported 6-iodoquinazoline (2) [synthesized according to example 5] (0.054 mmol, 0.54 mmol/g), 4-methylphenylboronic acid (0.5 mmol), Pd(PPh$_3$)$_4$ (20 mg), and 2 ml DMF are placed in a fritted polypropylene tube. The mixture is agitated at 80° got 24 h. After cooling to rt, the mixture is customary worked up for solid phase reactions. The solid supported 6-(4-methylphenyl)quinazoline and 2 ml of a mixture of H$_2$O, TFA and dichloromethane (1:49:50) are placed in a fritted polypropylene tube. The contents are shaken for 2 h at rt. The suspension is filtered and the resin is washed with dichloromethane (1 ml) and methanol (1 ml) respectively. Evaporation of the combined filtrates give (3-aminomethyl-cyclohexylmethyl)-{2-[2-(4-benzyloxy-phenyl)-vinyl]-6-4-tolyl-quinazolin-4-yl}-amine;

MS calc.: 568.8; found: 569.4.

Example 8

Analogously to example 1, 7-chloro-2-methylquinazolin-4-one is reacted with 3,4-bis-benzyloxy-benzaldehyde, chlorinated and reacted with C-(3-aminomethyl-cyclohexyl)-methylamine to obtain
(3-aminomethyl-cyclohexylmethyl)-{2-[2-(3,4-bis-benzyloxy-phenyl)-vinyl]-7-chloro-quinazolin-4-yl}-amine;

with N$^1$,N$^1$-diethyl-pentane-1,4-diamine to obtain
N$^4$-{2-[2-(3,4-bis-benzyloxy-phenyl)-vinyl]-7-chloro-quinazolin-4-yl}-N$^1$,N$^1$-diethyl-pentane-1,4-diamine;

with N$^1$,N$^1$-diethyl-propane-1,3-diamine to obtain
N'-{2-[2-(3,4-bis-benzyloxy-phenyl)-vinyl]-7-chloro-quinazolin-4-yl}-N,N-diethyl-propane-1,3-diamine;
MS calc.: 466.6; found: 467.3;

with 3-(4-methyl-piperazin-1-yl)-propylamine to obtain {2-[2-(3,4-bis-benzyloxy-phenyl)-vinyl]-7-chloro-quinazolin-4-yl}-[3-(4-methyl-piperazin-1-yl)-propyl]-amine;

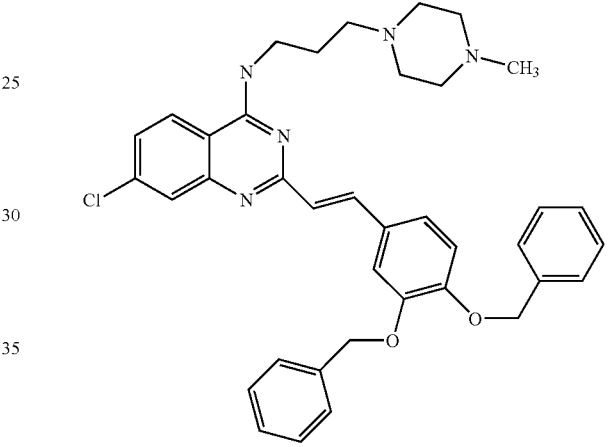

with 2,2-dimethyl-propane-1,3-diamine to obtain
N$^1$-{2-[2-(3,4-bis-benzyloxy-phenyl)-vinyl]-7-chloro-quinazolin-4-yl}-2,2-dimethyl-propane-1,3-diamine;

with 3-aminomethyl-benzylamine to obtain
(3-aminomethyl-benzyl)-{2-[2-(3,4-bis-benzyloxy-phenyl)-vinyl]-7-chloro-quinazolin-4-yl}-amine;

with heptane-1,7-diamine to obtain
N$^1$-{2-[2-(3,4-bis-benzyloxy-phenyl)-vinyl]-7-chloro-quinazolin-4-yl}-heptane-1,7-diamine;

with N$^1$-(3-amino-propyl)-N$^1$-methyl-propane-1,3-diamine to obtain
N$^1$-(3-{2-[2-(3,4-bis-benzyloxy-phenyl)-vinyl]-7-chloro-quinazolin-4-ylamino}-propyl)-N$^1$-methyl-propane-1,3-diamine;

with 3-[4-(3-amino-propyl)-piperazin-1-yl]-propylamine to obtain
{3-[4-(3-amino-propyl)-piperazin-1-yl]-propyl}-{2-[2-(3,4-bis-benzyloxy-phenyl)-vinyl]-7-chloro-quinazolin-4-yl}-amine;

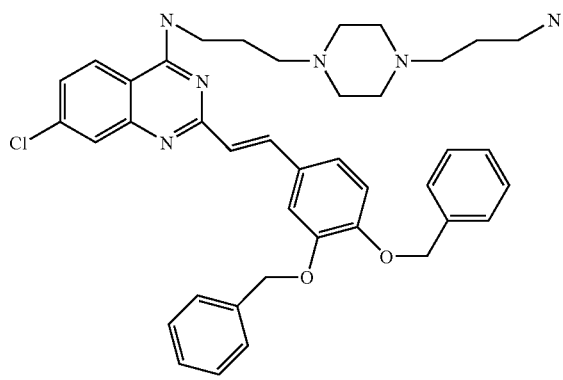

with C-cyclohexyl-methylamine to obtain
{2-[2-(3,4-bis-benzyloxy-phenyl)-vinyl]-7-chloro-quinazolin-4-yl}-cyclohexylmethyl-amine;

with 3-(3-amino-propoxy)-propylamine to obtain
[3-(3-amino-propoxy)-propyl]-{2-[2-(3,4-bis-benzyloxy-phenyl)-vinyl]-7-chloro-quinazolin-4-yl}-amine;

with 3-morpholin-4-yl-propylamine to obtain
{2-[2-(3,4-bis-benzyloxy-phenyl)-vinyl]-7-chloro-quinazolin-4-yl}-(3-morpholin-4-yl-propyl)-amine.

Example 9

Analogously to example 1, 7-chloro-2-methylquinazolin-4-one is reacted with benzaldehyde, chlorinated and reacted with 3-imidazol-1-yl-propylamine to obtain
(7-chloro-2-styryl-quinazolin-4-yl)-(3-imidazol-1-yl-propyl)-amine;

with $N^1,N^1$-diethyl-ethane-1,2-diamine to obtain
N'-(7-chloro-2-styryl-quinazolin-4-yl)-N,N-diethyl-ethane-1,2-diamine;

with $N^1,N^1$-diethyl-propane-1,3-diamine to obtain
N'-(7-chloro-2-styryl-quinazolin-4-yl)-N,N-diethyl-propane-1,3-diamine;

with 3-morpholin-4-yl-propylamine to obtain,
(7-chloro-2-styryl-quinazolin-4-yl)-(3-morpholin-4-yl-propyl)-amine;

with 1-(3-amino-propyl)-pyrrolidin-2-one to obtain
1-[3-(7-chloro-2-styryl-quinazolin-4-ylamino)-propyl]-pyrrolidin-2-one;

with 4-(2-amino-ethyl)-phenylamine to obtain
[2-(4-amino-phenyl)-ethyl]-(7-chloro-2-styryl-quinazolin-4-yl)-amine.

Analogously to example 1, 7-chloro-2-methylquinazolin-4-one is reacted with 4-bromo-benzaldehyde, chlorinated and reacted with $N^1,N^1$-diethyl-pentane-1,4-diamine to obtain
$N^4$-{2-[2-(4-bromo-phenyl)-vinyl]-7-chloro-quinazolin-4-yl}-$N^1,N^1$-diethyl-pentane-1,4-diamine;
MS calc.: 501.9; found: 501.9.

Analogously to example 1, 7-chloro-2-methylquinazolin-4-one is reacted with 3-phenyl-propenal, chlorinated and reacted with $N^1,N^1$-diethyl-pentane-1,4-diamine to obtain
$N^4$-[7-chloro-2-(4-phenyl-buta-1,3-dienyl)-quinazolin-4-yl]-$N^1,N^1$-diethyl-pentane-1,4-diamine;
MS calc.: 414.6; found: 415.3.

Example 10

1. Analogously to example 1, 2-methylquinazolin-4-one is reacted with 4-bromo-benzaldehyde and chlorinated to obtain 2-[2-(4-bromo-phenyl)-vinyl]-4-chloro-quinazoline.

2. The resin-bound carbamate (1) (4.8 g, 0.54 mmol/g) [synthesized analogously to example 5.1], 2-[2-(4-bromo-phenyl)-vinyl]-4-chloro-quinazoline (6.6 mmol), triethylamine (1 ml) and 50 ml DMF are placed in a fritted polypropylene tube. The mixture is stirred at 80° for 60 hrs. After cooling to rt, the resin is customary worked up for solid phase reactions. Resin bound carbamate (3) is obtained.

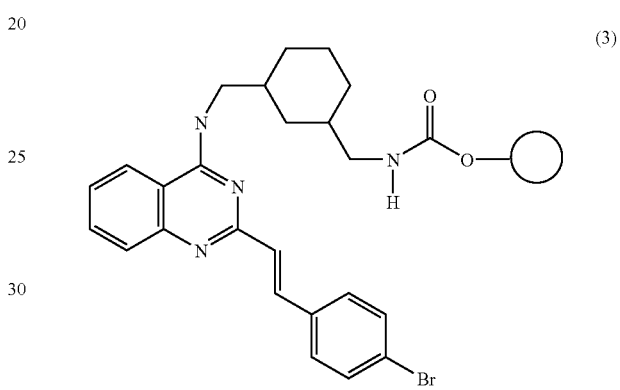

(3)

3. The solid supported 2-bromostyrylquinazoline (3) (0.054 mmol, 0.54 mmol/g), phenylboronic acid (0.5 mmol), Pd(PPh$_3$)$_4$ (20 mg), triethylamine (20 ml) and 2 ml DMF are placed in a fritted polypropylene tube. The mixture is agitated at 80° for 24 h. After cooling to rt, the mixture is customary worked up for solid phase reactions. The solid-supported 2-(2-biphenyl-4-yl-vinyl)-quinazoline and 2 ml of a mixture of H$_2$O, TFA and dichloromethane (1:49:50) is placed in a fritted polypropylene tube. The contents are shaken for 2 h at rt. The suspension is filtered and the resin is washed with dichloromethane (1 ml) and methanol (1 ml) respectively. Evaporation of the combined filtrates give (3-aminomethyl-cyclohexylmethyl)-[2-(2-biphenyl-4-yl-vinyl)-quinazolin-4-yl]-amine;
MS calc.: 448.6 found: 449.4.

Analogously to example 10, 2-methylquinazolin-4-one is reacted with 4-bromo-benzaldehyde, chlorinated, reacted with resin bound carbamate (4) [synthesized analogously to example 5.1]

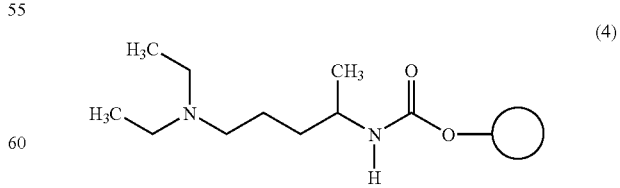

(4)

and phenylboronic acid to obtain
$N^4$-[2-(2-biphenyl-4-yl-vinyl)-7-chloro-quinazolin-4-yl]-$N^1,N^1$-diethyl-pentane-1,4-diamine;
MS calc.: 464.7 found: 465.2.

Example 11

Analogously to example 10, 7-chloro-2-methylquinazolin-4-one is reacted with 4-bromo-benzaldehyde, chlorinated, reacted with resin bound carbamate (1) and phenylboronic acid to obtain (3-aminomethyl-cyclohexylmethyl)-[2-(2-biphenyl-4-yl-vinyl)-7-chloro-quinazolin-4-yl]-amine;

MS calc.: 483.1; found: 483.3.

Analogously to example 10, 7-chloro-2-methylquinazolin-4-one is reacted with 4-bromo-benzaldehyde, chlorinated, reacted with resin bound carbamate (5) [synthesized analogously to example 5.1]

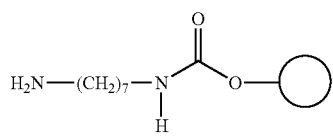
(5)

and phenylboronic acid to obtain
N$^1$-[2-(2-biphenyl-4-yl-vinyl)-7-chloro-quinazolin-4-yl]-heptane-1,7-diamine;

MS calc.: 471.0; found: 471.4;

with resin bound carbamate (6) [synthesized analogously to example 5.1]

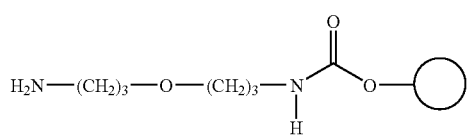
(6)

and phenylboronic acid to obtain
[3-(3-amino-propoxy)-propyl]-[2-(2-biphenyl-4-yl-vinyl)-7-chloro-quinazolin-4-yl]-amine;

MS calc.: 473.0; found: 473.3;

with resin bound carbamate (7) [synthesized analogously to example 5.1]

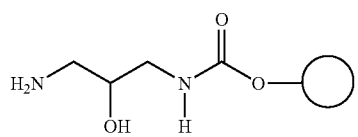
(7)

and phenylboronic acid to obtain
1-amino-3-[2-(2-biphenyl-4-yl-vinyl)-7-chloro-quinazolin-4-ylamino]-propan-2-ol;

MS calc.: 430.9; found: 431.2;

with resin bound carbamate (8) [synthesized analogously to example 5.1]

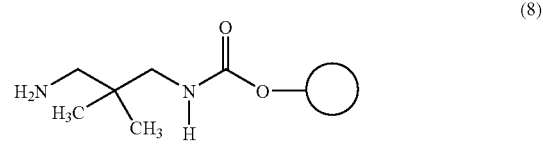
(8)

and phenylboronic acid to obtain
N$^1$-[2-(2-biphenyl-4-yl-vinyl)-7-chloro-quinazolin-4-yl]-2,2-dimethyl-propane-1,3-diamine;

with resin bound carbamate (9) [synthesized analogously to example 5.1]

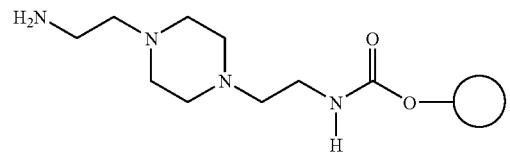
(9)

and phenylboronic acid to obtain
{3-[4-(3-amino-propyl)-piperazin-1-yl]-propyl}-[2-(2-biphenyl-4-yl-vinyl)-7-chloro-quinazolin-4-yl]-amine;

MS calc.: 541.1 found: 541.3;

with resin bound carbamate (10) [synthesized analogously to example 5.1]

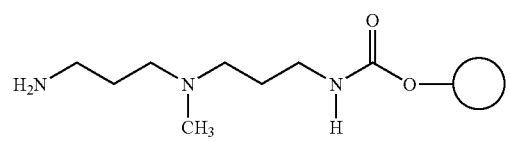
(10)

and phenylboronic acid to obtain
N$^1$-{3-[2-(2-biphenyl-4-yl-vinyl)-7-chloro-quinazolin-4-ylamino]-propyl}-N$^1$-methyl-propane-1,3-diamine;

MS calc.: 486.1; found: 486.2.

Example 12

Analogously to example 10, 6-iodo-2-methylquinazolin-4-one is reacted with 4-bromo-benzaldehyde, chlorinated, reacted with resin bound carbamate (1) and phenylboronic acid to obtain (3-aminomethyl-cyclohexylmethyl)-[2-(2-biphenyl-4-yl-vinyl)-6-iodo-quinazolin-4-yl]-amine;
MS calc.: 574.5 found: 575.2.

Analogously to example 10, 6-iodo-2-methylquinazolin-4-one is reacted with 4-bromo-benzaldehyde, chlorinated, reacted with resin bound carbamate (5) and phenylboronic acid to obtain
$N^1$-[2-(2-biphenyl-4-yl-vinyl)-6-iodo-quinazolin-4-yl]-heptane-1,7-diamine;
MS calc.: 562.5; found: 563.3;

with resin bound carbamate (6) and phenylboronic acid to obtain
[3-(3-amino-propoxy)-propyl]-[2-(2-biphenyl-4-yl-vinyl)-6-iodo-quinazolin-4-yl]-amine;
MS calc.: 564.5; found: 565.2;

with resin bound carbamate (7) and phenylboronic acid to obtain
1-amino-3-[2-(2-biphenyl-4-yl-vinyl)-6-iodo-quinazolin-4-ylamino]-propan-2-ol;
MS calc.: 522.4; found: 523.2;

with resin bound carbamate (8) and phenylboronic acid to obtain
$N^1$-[2-(2-biphenyl-4-yl-vinyl)-6-iodo-quinazolin-4-yl]-2,2-dimethyl-propane-1,3-diamine;
MS calc.: 534.4; found: 535.2;

with resin bound carbamate (9) and phenylboronic acid to obtain
{3-[4-(3-amino-propyl)-piperazin-1-yl]-propyl}-[2-(2-biphenyl-4-yl-vinyl)-6-iodo-quinazolin-4-yl]-amine;
MS calc.: 632.6; found: 633.2;

with resin bound carbamate (10) and phenylboronic acid to obtain
$N^1$-{3-[2-(2-biphenyl-4-yl-vinyl)-6-iodo-quinazolin-4-ylamino]-propyl}-$N^1$-methyl-propane-1,3-diamine;
MS calc.: 577.5; found: 578.1.

Example 13

Analogously to example 10, 7-chloro-2-methylquinazolin-4-one is reacted with 4-bromo-benzaldehyde, chlorinated, reacted with resin bound carbamate (1) and 2-methylphenylboronic acid to obtain
(3-aminomethyl-cyclohexylmethyl)-{7-chloro-2-[2-(2'-methyl-biphenyl-4-yl)-vinyl]-quinazolin-4-yl}-amine;
MS calc.: 497.1; found: 497.4;

2,4-dichlorophenylboronic acid
(3-aminomethyl-cyclohexylmethyl)-{7-chloro-2-[2-(2',4'-dichloro-biphenyl-4-yl)-vinyl]-quinazolin-4-yl}-amine;
MS calc.: 551.9; found: 551.3;

4-fluorophenylboronic acid
(3-aminomethyl-cyclohexylmethyl)-{7-chloro-2-[2-(4'-fluoro-biphenyl-4-yl)-vinyl]-quinazolin-4-yl}-amine;
MS calc.: 501.1; found: 501.4;

naphthylboronic acid
(3-aminomethyl-cyclohexylmethyl)-{7-chloro-2-[2-(4-naphthalen-1-yl-phenyl)-vinyl]-quinazolin-4-yl}-amine;
MS calc.: 533.1; found: 533.4;

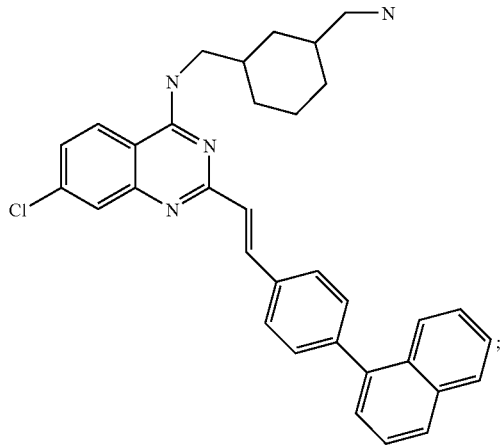

4-methoxyphenylboronic acid
(3-aminomethyl-cyclohexylmethyl)-{7-chloro-2-[2-(4'-methoxy-biphenyl-4-yl)-vinyl]-quinazolin-4-yl}-amine;
MS calc.: 513.1; found: 513.4;

3,4,5-trimethoxyphenylboronic acid
(3-aminomethyl-cyclohexylmethyl)-{7-chloro-2-[2-(3',4',5'-trimethoxy-biphenyl-4-yl)-vinyl]-quinazolin-4-yl}-amine;
MS calc.: 573.1; found: 573.4;

3-acetylaminophenylboronic acid
N-[4'-(2-{4-[(3-aminomethyl-cyclohexylmethyl)-amino]-7-chloro-quinazolin-2-yl}-vinyl)-biphenyl-3-yl]-acetamide;
MS calc.: 540.1; found: 540.4;

3-acetylphenylboronic acid
1-[4'-(2-{4-[(3-aminomethyl-cyclohexylmethyl)-amino]-7-chloro-quinazolin-2-yl}-vinyl)-biphenyl-3-yl]-ethanone;
MS calc.: 525.1; found: 525.4;

benzo[b]-thiophen-2-ylboronic acid
(3-aminomethyl-cyclohexylmethyl)-{2-[2-(4-benzo[b]thiophen-2-yl-phenyl)-vinyl]-7-chloro-quinazolin-4-yl}-amine;

3,5-bis-trifluoromethylphenylboronic acid
(3-aminomethyl-cyclohexylmethyl)-{2-[2-(3',5'-bis-trifluoromethyl-biphenyl-4-yl)-vinyl]-7-chloro-quinazolin-4-yl}-amine;

3-nitrophenylboronic acid
(3-aminomethyl-cyclohexylmethyl)-{7-chloro-2-[2-(3'-nitro-biphenyl-4-yl)-vinyl]-quinazolin-4-yl}-amine;
MS calc.: 528.1; found: 528.3;

thiophenylboronic acid
(3-aminomethyl-cyclohexylmethyl)-{7-chloro-2-[2-(4-thiophen-2-yl-phenyl)-vinyl]-quinazolin-4-yl}-amine;
MS calc.: 489.1; found: 489.4;

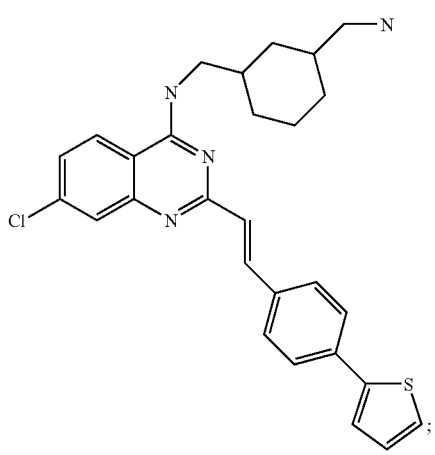

3-aminophenylboronic acid
(3-aminomethyl-cyclohexylmethyl)-{7-chloro-2-[2-(3'-amino-biphenyl-4-yl)-vinyl]-quinazolin-4-yl}-amine;
MS calc.: 498.1; found: 498.4;

3-isopropylphenylboronic acid
(3-aminomethyl-cyclohexylmethyl)-{7-chloro-2-[2-(3'-isopropyl-biphenyl-4-yl)-vinyl]-quinazolin-4-yl}-amine;
MS calc.: 525.1; found: 525.4;

pyridin-3-ylboronic acid
(3-aminomethyl-cyclohexylmethyl)-{7-chloro-2-[2-(4-pyridin-3-yl-phenyl)-vinyl]-quinazolin-4-yl}-amine;
MS calc.: 484.0; found: 484.4.

Example 14

Analogously to example 10, 7-chloro-2-methylquinazolin-4-one is reacted with 5-bromo-furan-2-carbaldehyde, chlorinated, reacted with resin bound carbamate (1) and
3-chlorophenylboronic acid to obtain
(3-aminomethyl-cyclohexylmethyl)-(7-chloro-2-{2-[5-(3-chloro-phenyl)-furan-2-yl]-vinyl}-quinazolin-4-yl)-amine;
MS calc.: 507.5 found: 507.8.

Example 15

Analogously to example 10, 7-chloro-2-methylquinazolin-4-one is reacted with 5-bromo-thiophene-2-carbaldehyde, chlorinated, reacted with resin bound carbamate (1) and thiophen-2-ylboronic acid to obtain
(3-aminomethyl-cyclohexylmethyl)-[2-(2-[2,2']bithiophenyl-5-yl-vinyl)-7-chloro-quinazolin-4-yl]-amine

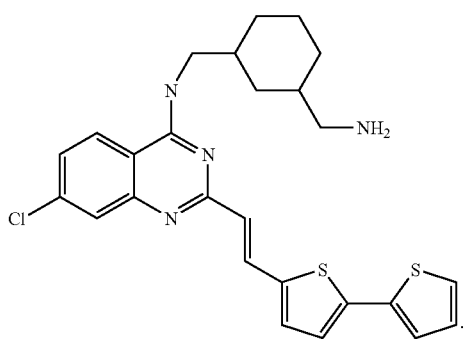

Analogously to example 10, 7-chloro-2-methylquinazolin-4-one is reacted with 5-bromo-thiophene-2-carbaldehyde, chlorinated, reacted with resin bound carbamate (4) and thiophenylboronic acid to obtain
$N^4$-[2-(2-[2,2']bithiophenyl-5-yl-vinyl)-7-chloro-quinazolin-4-yl]-$N^1$,$N^1$-diethyl-pentane-1,4-diamine;
MS calc.: 511.2; found: 511.1;

with resin bound carbamate (11)

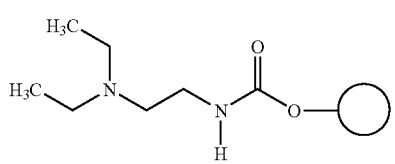
(11)

and thiophenylboronic acid to obtain
N'-[2-(2-[2,2']bithiophenyl-5-yl-vinyl)-7-chloro-quinazolin-4-yl]-N,N-diethyl-ethane-1,2-diamine;
MS calc.: 469.1; found: 469.1;

with resin bound carbamate (12)

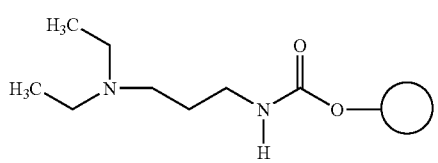
(12)

and thiophenylboronic acid to obtain
N'-[2-(2-[2,2']bithiophenyl-5-yl-vinyl)-7-chloro-quinazolin-4-yl]-N,N-diethyl-propane-1,3-diamine;
MS calc.: 483.1; found: 483.1;

with resin bound carbamate (13)

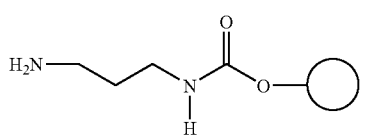
(13)

and thiophenylboronic acid to obtain
N¹-[2-(2-[2,2']bithiophenyl-5-yl-vinyl)-7-chloro-quinazolin-4-yl]-propane-1,3-diamine;
MS calc.: 427.0; found: 427.4;

with resin bound carbamate (14)

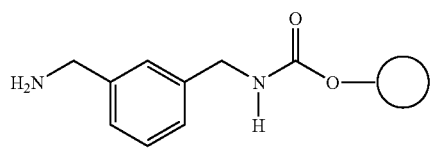

(14)

and thiophenylboronic acid to obtain
(3-aminomethyl-benzyl)-[2-(2-[2,2']bithiophenyl-5-yl-vinyl)-7-chloro-quinazolin-4-yl]-amine;
MS calc.: 489.1; found: 489.1;

with resin bound carbamate (5) and thiophenylboronic acid to obtain
N¹-[2-(2-[2,2']bithiophenyl-5-yl-vinyl)-7-chloro-quinazolin-4-yl]-heptane-1,7-diamine;
MS calc.: 483.1; found: 483.2;

with resin bound carbamate (10) and thiophenylboronic acid to obtain
N¹-{3-[2-(2-[2,2']bithiophenyl-5-yl-vinyl)-7-chloro-quinazolin-4-ylamino]-propyl}-N¹-methyl-propane-1,3-diamine;
MS calc.: 498.1; found: 498.1;

with resin bound carbamate (9) and thiophenylboronic acid to obtain
{3-[4-(3-amino-propyl)-piperazin-1-yl]-propyl}-[2-(2-[2,2']bithiophenyl-5-yl-vinyl)-7-chloro-quinazolin-4-yl]-amine;
MS calc.: 553.2 found: 553.2;

with resin bound carbamate (15)

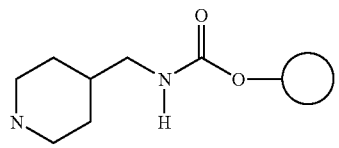

(15)

and thiophenylboronic acid to obtain
[2-(2-[2,2']bithiophenyl-5-yl-vinyl)-7-chloro-quinazolin-4-yl]-piperidin-4-ylmethyl-amine;
MS calc.: 467.1; found: 467.2;

with resin bound carbamate (6) and thiophenylboronic acid to obtain
[3-(3-amino-propoxy)-propyl]-[2-(2-[2,2']bithiophenyl-5-yl-vinyl)-7-chloro-quinazolin-4-yl]-amine;
MS calc.: 485.1; found: 485.2;

with resin bound carbamate (16)

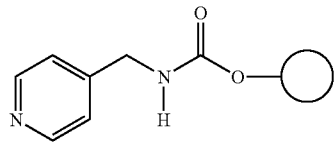

(16)

and thiophenylboronic acid to obtain
[2-(2-[2,2']bithiophenyl-5-yl-vinyl)-7-chloro-quinazolin-4-yl]-pyridin-4-ylmethyl-amine;
MS calc.: 461.0; found: 461.2.

Analogously to example 10, 6-iodo-2-methylquinazolin-4-one is reacted with 5-bromo-thiophene-2-carbaldehyde, chlorinated, reacted with resin bound carbamate (1) and thiophen-2-ylboronic acid to obtain
(3-aminomethyl-cyclohexylmethyl)-[2-(2-[2,2']bithiophenyl-5-yl-vinyl)-6-iodo-quinazolin-4-yl]-amine.

with resin bound carbamate (12) and thiophen-2-ylboronic acid to obtain
N'-[2-(2-[2,2']bithiophenyl-5-yl-vinyl)-6-iodo-quinazolin-4-yl]-N,N-diethyl-propane-1,3-diamine;
MS calc.: 574.5; found: 575.2.

The following examples relate to pharmaceutical preparations:

Example A

Injection Vials

A solution of 100 g of an active compound of the formula I and 5 g of disodium hydrogenphosphate is adjusted to pH 6.5 in 3 l of double-distilled water using 2N hydrochloric acid, sterile-filtered, dispensed into injection vials, lyophilized under sterile conditions and aseptically sealed. Each injection vial contains 5 mg of active compound.

Example B

Suppositories

A mixture of 20 g of an active compound of the formula I is melted with 100 g of soya lecithin and 1400 g of cocoa butter, poured into moulds and allowed to cool. Each suppository contains 20 mg of active compound.

Example C

Solution

A solution is prepared from 1 g of an active compound of the formula I, 9.38 g of $NaH_2PO_4.2H_2O$, 28.48 g of $Na_2HPO_4.12H_2O$ and 0.1 g of benzalkonium chloride in 940 ml of double-distilled water. The mixture is adjusted to pH 6.8, made up to 1 l and sterilized by irradiation. This solution can be used in the form of eye drops.

Example D

Ointment 500 mg of an active compound of the formula I is mixed with 99.5 g of petroleum jelly under aseptic conditions.

Example E

Tablets

A mixture of 1 kg of active compound of the formula I, 4 kg of lactose, 1.2 kg of potato starch, 0.2 g of talc and 0.1 kg of magnesium stearate is compressed in a customary manner to give tablets such that each tablet contains 10 mg of active compound.

Example F

Coated Tablets

Analogously to Example E, tablets are pressed which are then coated with a coating of sucrose, potato starch, talc, tragacanth and colorant in a customary manner.

Example G

Capsules 2 kg of active compound of the formula I are dispensed into hard gelatin capsules in a customary manner such that each capsule contains 20 mg of the active compound.

Example H

Ampules

A solution of 1 kg of active compound of the formula I in 60 ml of double-distilled water is sterile-filtered, dispensed into ampoules, lyophilized under sterile conditions and aseptically sealed. Each ampoule contains 10 mg of active compound.

What is claimed is:

1. Compounds of the formula I

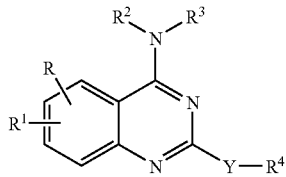

in which

R and $R^1$ are independently of each other H, A, $OR^5$, Hal, $N(R^5)_2$, $NO_2$, CN, $C(O)R^2$, $CON(R^5)_2$, $COOR^5$, allyl, CH=CH—$COOR^5$, CH=CHCON$(R^5)_2$, $SO_2A$ or phenyl, which is unsubstituted or mono-, di- or trisubstituted by A;

$R^2$ is H;

$R^3$ is —$(CH_2)_o$—Z—$(CH_2)_q$—$N(R^5)_2$;

$R^4$ is Ar;

$R^5$ is H or A;

Y is $(CH=CH)_n$;

Z is phenylene, cyclohexylene, —$NR^5$—, O, —CH(OH)—, —$CA_2$- or

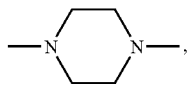

A is unbranched or branched alkyl having 1 to 6 carbon atoms;

Ar is phenyl or naphthyl, which is unsubstituted or mono-, di- or trisubstituted by A, $OR^5$, $CF_3$, $OCF_3$, Hal, CN, CHO, COA, $COOR^5$, $N(R^5)_2$, $NO_2$, $SO_2N(R^5)_2$;

Hal is F, Cl, Br or I;

n is 1 or 2;

o is 1, 2, 3, 4, 5, 6 or 7; and q is 1, 2, 3 or 4, or the pharmaceutically acceptable salts thereof.

2. Compounds of the formula I

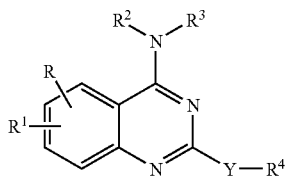

in which

R and $R^1$ are independently of each other H, A, $OR^5$, Hal, $N(R^5)_2$, $NO_2$, CN, $C(O)R^2$, $CON(R^5)_2$, $COOR^5$, allyl, CH=CH—$COOR^5$, CH=CHCON$(R^5)_2$, $SO_2A$ or phenyl, which is unsubstituted or mono-, di- or trisubstituted by A;

$R^2$ and $R^3$ are independently of each other H, A, cycloalkyl, -$Het^3$, —$(CH_2)_o$—$OR^5$, —$(CH_2)_o$—$OR^6$, —$(CH_2)_o$—$Het^1$, —$(CH_2)_o$—$NR^5$—$Het^1$, —$(CHA)_p$-$(CH_2)_o$—$N(R^5)_2$, —$(CH_2)_p$—$(CHA)_p$-$(CH_2)_m$—Ar, —$(CH_2)_o$—Z—$(CH_2)_q$—$N(R^5)_2$,

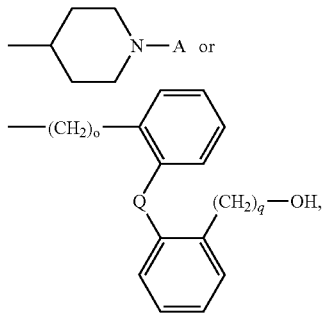

provided that $R^2$ and $R^3$ are not both H;

or $NR^2R^3$ together form a saturated monocyclic heterocyclic radical having 5 to 6 ring members, where 1 or 2 N ring atoms are present and the heterocyclic radical can be mono- or disubstituted by OH, Ar, OAr, arylalkyl;

$R^4$ is $Het^1$;

$R^5$ is H or A;

$R^6$ is benzo[1,3]dioxol-5-yl;

Q is O or S;

Y is $(CH=CH)_n$;

Z is phenylene, cyclohexylene, —$NR^5$—, O, —CH(OH)—, —$CA_2$- or

A is unbranched or branched alkyl having 1 to 6 carbon atoms;

Ar is phenyl, naphthyl or biphenyl, which in each case is unsubstituted or mono-, di- or trisubstituted by A, $OR^5$, cycloalkyloxy, O—$(CH_2)_p$-Ph, $CF_3$, $OCF_3$, Hal, CN, CHO, COA, $COOR^5$, $N(R^5)_2$, $NR^5$—COA, $NO_2$, $SO_2N(R^5)_2$ mor, $SO_2$-mor, 5-methyl-3-oxo-2,4-dihydropyrazol-2-yl, naphthyl, $Het^2$;

$Het^1$ is a saturated, partially or completely unsaturated mono- or bicyclic heterocyclic radical having 5 to 10 ring members, where 1 to 2 N, 1 to 2 S, 1 to 2 O ring atoms, or combinations thereof, are present and which is unsubstituted or mono- or disubstituted wherein each substituent is selected from A, Hal, $OR^5$, $CF_3$, $OCF_3$, $N(R^5)_2$, carbonyl oxygen, $COOR^5$, $Het^2$, benzyl and phenyl, wherein benzyl and phenyl are unsubstituted or mono-, di- or trisubstituted by A, $OR^5$, $CF_3$, $OCF_3$, Hal, CN, $COOR^5$, $N(O)_2$, $NO_2$, $SO_2N(R^5)_2$;

$Het^2$ is an unsaturated mono- or bicyclic heterocyclic radical having 5 to 10 ring members, where 1 to 2 N, 1 to 2 S, 1 to 2 O ring atoms, or combinations thereof, are present, and which is unsubstituted or mono- or disubstituted by A, Hal, $OR^5$, $CF_3$, $OCF_3$, $N(R^5)_2$, $COOR^5$;

$Het^3$ is a partially or completely unsaturated mono- or bicyclic heterocyclic radical having 5 to 10 ring members, where 1 or 2 N ring atoms are present, and which is unsubstituted or is mono- or disubstituted by A, Hal, $OR^5$, $CF_3$, $OCF_3$, $N(O)_2$, $SO_2A$, $COOR^5$, or combinations thereof, provided that the heterocyclic radical is not bonded via an N atom;

Hal is F, Cl, Br or I;

mor is morpholin-4-yl;

Ph is phenyl;

n is 1 or 2;

m is 0, 1, 2, 3, 4, 5 or 6;

o is 1, 2, 3, 4, 5, 6 or 7;

p is 0, 1, 2, 3 or 4;

q is 1, 2, 3 or 4;

or the pharmaceutically acceptable salts thereof.

3. A compound which is
a) N'-[2-(2-[2,2']bithiophenyl-5-yl-vinyl)-6-iodo-quinazolin-4-yl]-N,N-diethyl-propyl-1,3-diamine;
b) (3-aminomethyl-cyclohexylmethyl)-[2-(2-[2,2']bithiophenyl-5-yl-vinyl)-7-chloro-quinazolin-4-yl]amine;

or the physiologically tolerable salts thereof.

* * * * *